(12) United States Patent
Gilbert et al.

(10) Patent No.: US 9,245,090 B2
(45) Date of Patent: Jan. 26, 2016

(54) FINGERPRINT FOR CELL IDENTITY AND PLURIPOTENCY

(75) Inventors: David M. Gilbert, Tallahassee, FL (US); Tyrone Ryba, Tallahassee, FL (US); Jinfeng Zhang, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 47 days.

(21) Appl. No.: 13/595,017

(22) Filed: Aug. 27, 2012

(65) Prior Publication Data

US 2014/0149048 A1 May 29, 2014

Related U.S. Application Data

(60) Provisional application No. 61/527,771, filed on Aug. 26, 2011.

(51) Int. Cl.
G06F 19/10 (2011.01)
G06F 19/00 (2011.01)
G06F 19/24 (2011.01)

(52) U.S. Cl.
CPC ...................................... *G06F 19/24* (2013.01)

(58) Field of Classification Search
None
See application file for complete search history.

(56) References Cited

PUBLICATIONS

Dimov et al. (Journal of Computational and Applied Mathematics (1998) vol. 92:15-35).*
Weddington, N., et al., "ReplicationDomain: a Visualization Tool and Comparative Database for Genome-Wide Replication Timing Data," BMC Bioinformatics, vol. 9, pp. 1-11, 2008.
Woodfine, K., et al., "Replication Timing of the Human Genome," Hum Mol Genet, vol. 13, No. 2, pp. 191-202, 2003.
Yaffe, E., et al., "Comparative Analysis of DNA Replication Timing Reveals Conserved Large-Scale Chromosomal Architecture," PLoS Genetics, vol. 6, No. 7, pp. 1-12, 2010.
Yokochi, T., et al., "G9a selectively represses a class of late-replicating genes at the nuclear periphery," PNAS, vol. 106, No. 46, pp. 19363-19368, 2009.
Attwood, J.T., et al., "DNA methylation and the regulation of gene transcription," CMLS, Cell Mol. Life Sci., vol. 59, pp. 241-257, 2002.
Burton, G.R., et al., "Microarray analysis of gene expression during early adipocyte differentiation," Gene, vol. 293, pp. 21-31, 2002.
Jones, P.A., et al., "Cancer Epigenetics Comes of Age," Nature Genetics, vol. 21, pp. 163-167, 1999.
Laird, P.W., "The Power and the Promise of DNA Methylation Markers," Nature Reviews Cancer, vol. 3, pp. 256-266, 2003.
Angst, B.D., et al., "The Cadherin Superfamily: Diversity in Form and Function," Journal of Cell Science, vol. 114, No. 4, pp. 629-641, 1992.
Barlesi, F., et al., "Global Histone Modifications Predict Prognosis of Resected Non-Small-Cell Lung Cancer," Journal of Clinical Oncology, vol. 25, pp. 4358-4864, 2007.
Baron, U., et al., "DNA Methylation Analysis as a Tool for Cell Typing," Epigenetics, vol. 1, No. 1, pp. 55-60, 2006.
Berezney, R., et al., "Heterogeneity of Eukaryotic Replicons, Replicon Clusters, and Replication Foci," Chromosoma, vol. 108, pp. 471-484, 2000.
Chang, H. H., et al., "Transcriptome-wide noise controls lineage choice in mammalian progenitor cells," Nature, vol. 453, pp. 544-547, 2008.
Cover, T., et al., "Nearest Neighbor Pattern Classification," IEEE Trans. Inf. Theory, vol. 13, No. 1, pp. 21-27, 1967.
Derisi, J.L., et al., "Exploring the Metabolic and Genetic Control of Gene Expression on a Genomic Scale," Science, vol. 278, pp. 680-686, 1997.
Desprat, R., et al., "Predictable Dynamic Program of Timing of DNA Replication in Human Cells," Genome Res. vol. 19, pp. 2288-2299, 2009.
Efroni, S., et al., "Stem Cells do Play with Dice," Cell Cycle, vol. 8, pp. 43-48, 2009.
Elsheikh, S.E., et al., "Global Histone Modiciations in Breast Cancer Correlate with Tumor Phenotypes, Prognostic Factors, and Patience Outcome," Cancer Res. vol. 69, pp. 3802-3809, 2009.
Esteller, M., "CpG Island Hypermethylation and Tumor Suppressor Genes: a Booming Present, a Brighter Future," Oncogene, vol. 21, pp. 5427-5440, 2002.
Farkash-Amar, S., et al., "Global Organization of Replication Time Zones of the Mouse Genome," Genome Research, vol. 18, pp. 1562-1670, 2008.
Figueroa, M.E., et al., "Genome-Wide Epigenetic Analysis Delineates a Biologically Distinct Immature Acute Leukemia with Myeloid/T-Lymphoid Features," Blood, vol. 113, pp. 2795-2804, 2009.
Gentleman, R.C., et al., "Bioconductor: Open Software Development for Computational Biology and Bioinformatics," Genome Biology, vol. 5, No. 1, pp. R80-R80.16, 2004.
Gerbaulet, S.P., et al., "Downregulation of histone H4 gene transcription during postnatal development in transgenic mice and at the onset of differentiation in transgenically derived calvarial osteoblast cultures," J. Cell Biochem. vol. 49, No. 2, pp. 137-147, 1992.
Ginis, I., et al., "Differences Between Human and Mouse Embryonic Stem Cells," Developmental Biology, vol. 269, pp. 360-380, 2004.
Hanna, J., et al., "Human embryonic stem cells with biological and epigenetic characteristics similar to those of mouse ESCs," PNAS, vol. 107, No. 20, pp. 9222-9227, 2010.
Hastings, W.K., "Monte Carlo Sampling Methods Using Markov Chains and Their Applications," Biometrika, vol. 57, No. 1, pp. 97-109, 1970.
Heng, J-C, D., et al., "Transcription Factors for the Modulation of Pluripotency and Reprogramming," Cold Spring Harbor Symp Quant Biol, vol. 75, pp. 237-244, 2010.
Hiratani, I., et al., "Global Reorganization of Replication Domains During Embryonic Stem Cell Differentiation," PLoS Biology, vol. 6, No. 10, pp. 2220-2236, 2008.

(Continued)

*Primary Examiner* — Lori A Clow
(74) *Attorney, Agent, or Firm* — Alchemy-Partners, PC

(57) ABSTRACT

A method for determining a replication timing footprint comprises the following steps: (a) selecting a set of chosen regions of the replication timing profile of a chromosome of an individual, (b) choosing a set of selected regions from the set of chosen regions to form a set of selected regions and a set of unused regions, (c) conducting a iterative algorithm on the set of selected regions until a domain number for the set of selected regions has decreased to a predetermined minimum, (d) determining a replication timing footprint based the set of selected regions after step (c) has been conducted, and (e) displaying the replication timing footprint to a user.

15 Claims, 21 Drawing Sheets

(56) References Cited

PUBLICATIONS

Hiratani, I., et al., "Differentiation-induced replication-timing changes are restricted to AT-rich/long interspersed nuclear element (LINE)-rich isochores," Proc. Natl. Acad. Sci. U.S.A. vol. 101, No. 48, pp. 16861-16866, 2004.

Hiratani, I., et al., "Genome-wide dynamics of replication timing revealed by in vitro models of mouse embryogenesis," Genome Res. vol. 20, pp. 155-169, 2009.

Hou, J., et al., "Gene Expression-Based Classification of Non-Small Cell Lung Carcinomas and Survival Prediction," PLoS One, vol. 5, No. 4, pp. 1-12, 2010.

Jullien, J., et al., "Characterization of somatic cell nuclear reprogramming by oocytes in which a linker histone is required for pluripotency gene reactivation," PNAS, vol. 107, No. 12, pp. 5483-5488, 2010.

Koch, C.M., et al., "The Landscape of Histone Modifications Across 1% of the Human Genome in Five Human Cell Lines," Genome Research, vol. 17, pp. 691-707, 2007.

Maherali, N., et al., "Directly Reprogrammed Fibroblasts Show Global Epigenetic Remodeling and Widespread Tissue Contribution," Cell Stem Cell, vol. 1, pp. 55-70, 2007.

Marsit, C.J., et al., "DNA Methylation Array Analysis Identifies Profiles of Blood-Derived DNA Methylation Associated With Bladder Cancer," Journal of Clinical Oncology, vol. 29, No. 9, pp. 1133-1139, 2011.

McLean, A.B., et al., "Activin A Efficiently Specifies Definitive Endoderm from Human Embryonic Stem Cells Only When Phosphatidylinositol 3-Kinase Signaling Is Suppressed," Stem Cells, vol. 25, pp. 29-38, 2007.

Meshorer, E., et al., "Hyperdynamic Plasticity of Chromatin Proteins in Pluripotent Embryonic Stem Cells," Developmental Cell, vol. 10, pp. 105-116, 2006.

Metropolis, N., et al., "Equation of State Calculations by Fast Computing Machines," Journal of Chemical of Physics, vol. 21, pp. 1087-1092, 1953.

Miller, et al., "Switching from life to death: The Miz-ing Link between Myc and p53," Cancer Cell, vol. 2, pp. 353-361, 2002.

Murphy, D., "Principles, Problems, and Prospects," Advances in Physiology Education, vol. 26, No. 4, pp. 256-270, 2002.

Nadon, R., et al., "Statistical issues with microarrays: processing and analysis," TRENDS in Genetics, vol. 18, No. 5, pp. 265-271, 2002.

Park, I.H., et al., "Reprogramming of human somatic cells to pluripotency with defined factors," Nature, vol. 451, pp. 141-146, 2008.

Pope, B.D., "Domain-wide regulation of DNA replication timing during mammalian development," Chromosome Research, vol. 18, pp. 127-136, 2010.

The R Development Core Team, "R: A Language and Environment for Statistical Computing," R Foundation for Statistical Computing ISBN vol. 3, pp. 1-1731, 2008.

Ryba, T., et al., "Evoluationarily Conserved Replication Timing Profiles Predict Long-Range Chromatin Interactions and Distinguish Closely Related Cell Types," Genome Research, vol. 20, pp. 761-770, 2010.

Ryba, T., et al., "Genome-Scale Analysis of Replication Timing: From Bench to Bioinformatics," Nature Protocols, vol. 6, No. 6, pp. 870-895, 2011.

Ryba, T., et al., "Replication Timing: A Fingerprint for Cell Identity and Pluripotency," PLoS Computational Biology, vol. 7, No. 10, pp. 1-13, 2011.

Sano, K., et al., "Protocadherins: A Large Family of Cadherin-Related Molecules in Central Nervous System," The EMBO Journal, vol. 12, No. 6, pp. 2249-2256, 1993.

Schubeler, D., et al., "Genome-Wide DNA Replication Profile and *Drosophila melanogaster*: a Link Between Transcription and Replication Timing," Nature Genetics, vol. 32, pp. 438-442, 2002.

Schulz, T.C., et al., "Differentiation of Human Embryonic Stem Cells to Dopaminergic Neurons in Serum-Free Suspension Culture," Stem Cells vol. 22, pp. 1218-1238, 2004.

Silva, J., et al. "Capturing Pluripotency," Cell, vol. 132, pp. 532-536, 2008.

Sotiriou, C., et al., "Gene-Expression Signatures in Breast Cancer," The New England Journal of Medicine, vol. 360, pp. 790-800, 2009.

Spellman, P.T., et al., "Comprehensive Identification of Cell Cycle-Regulated Genes of the Yeast *Saccharomyces cerevisiae* by Microarray Hybridization," Molecular Biology Cell, vol., 9, No. 12, pp. 3273-3297, 1998.

Takahashi, K., et al., "Induction of Pluripotent Stem Cells from Mouse Embryonic and Adult Fibroblast Cultures by Defined Factors," Cell, vol. 126, pp. 663-676, 2006.

Tesar, P.J., "New Cell Lines from Mouse Epiblast Share Defining Featurs with Human Embryonic Stem Cells," Nature, vol. 448, pp. 196-199, 2007.

Toyooka, Y., et al., "Identification and Characterization of Subpopulations in Undifferentiated ES Cell Culture," Development vol. 135, pp. 909-918, 2008.

Voss, T.C., "Combinatorial probabilistic chromatin interactions produce transcriptional heterogeneity," Journal of Cell Science, vol. 122, pp. 345-356, 2009.

Weber, M., et al., "Distribution, silencing potential and evolutionary impact of promoter DNA methylation in the human genome," Nature Genetics, vol. 39, pp. 457-466, 2007.

\* cited by examiner

Table 1

Mouse datasets

| Cell line | Cell type | Description | Culture/differentiation protocol | RT dataset reference |
|---|---|---|---|---|
| D3 | ESC | Embryonic stem cells | Doetschman et al. (1985) | Hiratani et al. (2008) |
| TT2 | ESC | Embryonic stem cells | Yagi et al. (1993) | Hiratani et al. (2008) |
| 46C | ESC | Embryonic stem cells | Ying et al. (2003) | Hiratani et al. (2008) |
| D3 | EBM3 | 3-day NPC intermediate | Rathjen et al. (2002) | Hiratani et al. (2010) |
| D3 | EPL | Early primitive endoderm-like | Rathjen et al. (2002) | Hiratani et al. (2010) |
| D3 | EBM6 | 6-day NPC intermediate | Rathjen et al. (2002) | Hiratani et al. (2010) |
| EpiSC5 | EpiSC | Epiblast stem cells (male) | Tesar et al. (2007) | Hiratani et al. (2010) |
| EpiSC7 | EpiSC | Epiblast stem cells (female) | Tesar et al. (2007) | Hiratani et al. (2010) |
| D3 | NPC | Neural precursor cells | Rathjen et al. (2002) | Hiratani et al. (2008) |
| TT2 | NPC | Neural precursor cells | Ying et al. (2003) | Hiratani et al. (2008) |
| 46C | NPC | Neural precursor cells | Ying et al. (2003) | Hiratani et al. (2008) |
| iPS | iPSC | Induced pluripotent stem cells (m) | Hanna et al. (2007) | Hiratani et al. (2008) |
| 1A2 | piPSC | Induced pluripotent stem cells (f) | Maherali et al. (2007) | Hiratani et al. (2010) |
| 1B3 | piPSC | Induced pluripotent stem cells (f) | Maherali et al. (2007) | Hiratani et al. (2010) |
| 1D4 | piPSC | Partial induced pluripotent stem cells (f) | Maherali et al. (2007) | Hiratani et al. (2010) |
| 2D4 | iPSC | Partial induced pluripotent stem cells (f) | Maherali et al. (2007) | Hiratani et al. (2010) |
| V3 | piPSC | Partial induced pluripotent stem cells (f) | K.Plath, unpubl. | Hiratani et al. (2010) |
| EBS | Mesoderm | Goosecoid(Gsc)+Sox17− mesoderm | Yasunaga et al. (2005) | Hiratani et al. (2010) |
| EBS | Endoderm | Gsc+Sox17+ endoderm | Yasunaga et al. (2005) | Hiratani et al. (2010) |
| V3 | MEF | Mouse embryonic fibroblasts | K.Plath, unpubl. | Hiratani et al. (2010) |
| 1185a | Myoblast | Fetal myoblast cells | C. Thornton, unpubl. | Hiratani et al. (2010) |

Table 2

Human datasets

| Cell line | Cell type | Description | Culture/differentiation protocol | RT dataset reference |
|---|---|---|---|---|
| BG01 | ESC | Embryonic stem cells | Wang et al. (2007) | Ryba et al. (2010) |
| BG02 | ESC | Embryonic stem cells | Wang et al. (2007) | Ryba et al. (2010) |
| H7 | ESC | Embryonic stem cells | Wang et al. (2007) | Ryba et al. (2010) |
| H9 | ESC | Embryonic stem cells | Wang et al. (2007) | Ryba et al. (2010) |
| iPS4 | iPSC | Induced pluripotent stem cells | Park et al. (2008) | Ryba et al. (2010) |
| iPS5 | iPSC | Induced pluripotent stem cells | Park et al. (2008) | Ryba et al. (2010) |
| BG03 | NPC | Neural precursor cells | Schulz et al. (2004) | Ryba et al. (2010) |
| C0202 | Lymphoblast | Lymphoblastoid cells | Woodfine et al. (2004) | Ryba et al. (2010) |
| GM06990 | Lymphoblast | Lymphoblastoid cells | Koch et al. (2007) | Ryba et al. (2011) |
| BG02 | Endomesoderm | 2-day definitive endoderm intermediate | Maclean et al. (2007) | Ryba et al. (2011) |
| BG02 | Endoderm | definitive endoderm | Maclean et al. (2007) | Ryba et al. (2011) |
| BG02 | Mesoderm | ISL1+ mesoderm | Maclean et al. (2007) | Ryba et al. (2011) |
| BG02 | Smooth muscle | Smooth muscle | Maclean et al. (2007) | Ryba et al. (2011) |

*FIG. 4*

Table 3

| Human cell type classification using different window sizes | | | | |
|---|---|---|---|---|
| Window size | 50kb | 100kb | 200kb | 400kb |
| Number of windows | 50564 | 25282 | 12625 | 6321 |
| Probes per region | 14 | 29 | 58 | 114 |
| Average distance between like cell types | 0.88 | 0.95 | 0.92 | 0.88 |
| Average distance between distinct cell types | 5.23 | 5.28 | 5.37 | 4.80 |
| Distance ratio | 5.92 | 5.55 | 5.81 | 5.45 |
| Classification accuracy | 31/31 | 31/31 | 31/31 | 31/31 |
| LOOCV accuracy | 31/31 | 31/31 | 31/31 | 31/31 |

FIG. 7

Table 4

FIG. 27

SEQUENCE LISTING

<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acatgggcgt gcaatcccca                                                     20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggccctggtt gctaggtgcg                                                     20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcaaaacggc caacggctga                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcctgccag tgctgagagg                                                     20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttggcccacg tgtgggaga                                                      20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgaccccctc ccaggcagtg                                                     20

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgacccctgc acccaccaca                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gccgcagctg gaaaaggggt                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcgttgccct ttgccaccac                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctgcagcct ccacctgcaa                                               20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agccctgaaa ggtgagcccc a                                             21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gggtgggagg gggctgctaa                                               20
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcacgttgca gatgcactgc g                                              21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tggatgggtc acgtgtggcg                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gttgctcacc acgggaggcc                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccacaagcca gccgacggag                                                20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gggtttccgg gcaggtggtg                                                20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agccccggct ttcctcccctt                                               20

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccgcctcttc ccaccccact                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggcctggcag gggttttgct                                                   20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtggggattg actgcactgc ca                                                22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcaatgcccc ctcccccaac a                                                 21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtgcccagcg gccagtgtag                                                   20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctgagtgtgg cgcctgtggg                                                   20

<210> SEQ ID NO 25
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgccctatcc cgggactgct                                                   20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctgtgtctg cttcccccac c                                                 21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaggccagtt gcaggccctg                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caccccaacg gcgcatggtt                                                   20

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aggcagcact gcggtaatat gct                                               23

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gggctgcagt gggttctgcc                                                   20

<210> SEQ ID NO 31
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtggcagcta cacggccagg                                                  20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggaagcccca aacccaggca                                                  20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tctgtgcggg cctgaagggg                                                  20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agcggccaca tcttgcaggt                                                  20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggcaccacga gggagatgcg                                                  20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cccggcagtg ggagagacga                                                  20

<210> SEQ ID NO 37
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37 ctggccctc ctcacctccg                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggcacaccag gcagcacctc                                                   20

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acacatttgc tgagggccca ct                                                22

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
actgtcccat cctgcggcct                                                   20
```

FINGERPRINT FOR CELL IDENTITY AND PLURIPOTENCY

CROSS-REFERENCE TO RELATED APPLICATIONS

This application claims benefit of priority to U.S. Provisional Patent Application No. 61/527,771, entitled, "FINGERPRINT FOR CELL IDENTITY AND PLURIPOTENCY, filed Aug. 26, 2011, which is incorporated by reference in its entirety.

GOVERNMENT INTEREST STATEMENT

The United States Government may have rights in this invention pursuant to National Institutes of Health (NIH) Grant No. GM085354.

SEQUENCE LISTING

The instant application contains a Sequence Listing which has been submitted in ASCII format via EFS-WEB and is hereby incorporated by reference in its entirety. Said ASCII copy, created on Oct. 11, 2012, is named 74623002.txt and is 9,458 bytes in size.

BACKGROUND

1. Field of the Invention

The present invention relates to cell characterization techniques.

2. Related Art

Conventional mechanisms to classify or identify cells involve a variety of heterogeneous biochemical and molecular procedures. For example, morphology-based approaches (e.g., histology) rely on microscopic examination of cell shape and features to determine cell type. This approach is useful in cases in which cells display a distinctive shape (e.g., long axons in neurons) and/or an easily recognizable feature (e.g., a lipid vesicle stained for fats), but most cells are difficult to distinguish based on their appearance alone. Histology-based procedures for cell identification also require a highly trained person, making them impossible to apply in a high-throughput manner.

Protein-based approaches, including biochemical and/or immunological techniques, involve detection of specific proteins that may indicate a particular cell type. A protein may be recognized by an antibody specific for such protein present either on the cell surface (e.g., by immunohistology) or in extracts or samples from disintegrated cells (e.g., by immunoblotting or ELISA). These assays are generally sensitive, fast and simple. However, because each antibody recognizes only one particular protein antigen, such approaches generally do not provide sufficient information to distinguish various types of cells. In other words, a single protein marker is rarely a guarantee of a particular cell type. On the other hand, larger-scale protein detection methods (e.g., proteomics) suffer from insufficient sensitivity and a lack of capability for automation.

RNA-based approaches are based generally on the detection of mRNA as a reflection of gene expression that may be indicative of a particular cell type and may be performed individually or using an array system. See, e.g., Spellman et al., *Mol. Biol. Cell* 9:3273-97 (1998); DeRisi et al., *Science* 278:680-86 (1997); Burton et al., *Gene* 293:21-31 (2002). Indeed, these technologies can produce a great deal of information about the overall pattern of gene expression of a cell. However, the decisive drawback of this system is the instability of RNA. Every experiment with RNA must take into account possible degradation of RNA that may occur during sample collection, storage and experimentation. This is especially problematic when working with archived samples (e.g., preserved biopsies) or with limited amounts of cellular material. A further problem with RNA-based approaches is that mRNA fluctuates in response to temporary changes in environmental conditions. In addition, it has been demonstrated recently that mouse embryonic stem cells (mESCs) display considerable cell-to-cell heterogeneity in the expression of certain pluripotency-specific marker genes. See, e.g., Silva et al., "Capturing pluripotency," *Cell* 132:532-536 (2008); and Toyooka et al., "Identification and characterization of subpopulations in undifferentiated ES cell culture," *Development* 135:909-18 (2008).

Therefore, RNA-based approaches for cell identification are limited by perturbations in gene expression caused by transient cell culture conditions, cell-to-cell heterogeneity in gene expression, and random degradation of mRNA in cell-derived extracts or samples that adversely affect the robustness, reproducibility and interpretation of such techniques. As a result, biological and stochastic variability must be countered by intense bioinformatic analysis. In general, RNA-based arrays are useful discovery tools, but they are not yet widely applicable as a clinical or large-scale assay method for the identification of cells. See, e.g., Miller et al., *Cancer Cell* 2:353-61 (2002); Nadon et al., *Trends Genet* 18:265-71 (2002); Murphy D, *Adv Physiol Educ.,* 26:256-70 (2002).

In recent years, some markers for epigenetic modifications to chromatin, such as DNA methylation and histone acetylation, have been used to study and distinguish cells. Such approaches are based on the fact that higher organisms must impose and maintain different patterns of gene expression in various types of tissues and/or cells despite having essentially the same DNA sequence encoded by the genome of all cell types within the body of an individual. This is achieved largely through changes in chromatin structure caused in part by chemical modification of chromatin. Generally speaking, the most condensed chromatin domains, known as heterochromatin, are inaccessible to DNA binding factors and tend to be transcriptionally silent, whereas more extended chromatin domains, known as euchromatin, correspond to more accessible portions of the genome that tend to be transcriptionally active.

Therefore, assaying for various epigenetic modifications to chromatin within a collection of cells may provide a basis for distinguishing not only different types of cells, but normal vs. transformed cells. For example, aberrant methylation of DNA frequently accompanies the transformation event from healthy to cancerous cells. Indeed, there are examples where specific methylation status may be used to identify and/or distinguish various forms of cancer (see, e.g., Jones et al., *Nature Genetics* 21:163-167 (1999); Esteller et al., *Oncogene* 21:5427-5440 (2002); Laird et al., *Nature Reviews Cancer* 3:253-66 (2003)), as well as different stages and lineage commitments of normal cells (see, e.g., Attwood et al., *CMLS* 59:241-57 (2002)). However, these techniques based on epigenetic chemical modifications to identify cell states are limited by the fact that (1) they require very high resolution (200 bp nucleosomal units), (2) they reflect dynamic chromatin states that can change or become heterogeneous within a homogeneous cell type, (3) there is a large diversity of histone modifications that would need to be individually investigated to gain a comprehensive profile, and (4) these rely on the use of different and expensive antibodies and other reagents that would create challenges for high-throughput analysis.

Accordingly, new and improved methods for identifying and/or distinguishing cells are still needed.

SUMMARY

According to a first broad aspect, the present invention provides a method comprising the following steps: (a) selecting a set of chosen regions of a replication timing profile of a chromosome of an individual; (b) choosing a set of selected regions from the set of chosen regions to form a set of selected regions and a set of unused regions; (c) conducting a iterative algorithm on the set of selected regions until a domain number for the set of selected regions has decreased to a predetermined minimum; (d) determining a replication timing fingerprint based on the set of selected regions after step (c) has been and (e) displaying the replication timing fingerprint to a user; wherein each of the chosen regions of the replication timing profile correspond to a segment of the chromosome that is 150 kb to 200 kb in size; and wherein iterative algorithm of step (c) comprises randomly selecting between the following three moves: (i) adding an unused region from the set of unused regions to the set of selected regions; (ii) removing a removed selected region from the set of selected regions so that the removed selected region becomes an unused region of the set of unused regions; and (iii) swapping a swapped unused region of the set of unused regions with a swapped selected region of the set of selected regions so that the swapped unused region becomes a selected region of the set of selected regions and so that the swapped selected region becomes an unused region of the set of unused regions.

According to a second broad aspect, the present invention provides a machine-readable medium having stored thereon sequences of instructions, which when executed by one or more processors, cause one or more electronic devices to perform a set of operations comprising the following steps: (a) selecting a set of chosen regions of a replication timing profile of a chromosome of an individual; (b) choosing a set of selected regions from the set of chosen regions to form a set of selected regions and a set of unused regions; (c) conducting a iterative algorithm on the set of selected regions until a domain number for the set of selected regions has decreased to a predetermined minimum; (d) determining a replication timing fingerprint based on the set of selected regions after step (c) has been conducted; and (e) displaying the replication timing fingerprint to a user; wherein each of the chosen regions of the replication timing profile correspond to a segment of the chromosome that is 150 kb to 200 kb in size; and wherein iterative algorithm of step (c) comprises randomly selecting between the following three moves: (i) adding an unused region from the set of unused regions to the set of selected regions (ii) removing a removed selected region from the set of selected regions so that the removed selected region becomes an unused region of the set of unused regions and (iii) swapping a swapped unused region of the set of unused regions with a swapped selected region of the set of selected regions so that the swapped unused region becomes a selected region of the set of selected regions and so that the swapped selected region becomes an unused region of the set of unused regions.

BRIEF DESCRIPTION OF THE DRAWINGS

The accompanying drawings, which are incorporated herein and constitute part of this specification, illustrate exemplary embodiments of the invention and, together with the general description given above and the detailed description given below, serve to explain the features of the invention.

FIG. 4 shows an experimental mouse dataset (Table 1) and an experimental human dataset (Table 2).

FIG. 7 shows a table providing a summary of algorithm performance using window sizes of 50 kb, 100 kb, 200 kb and 400 kb.

FIG. 27 provides a table showing primers (SEQ ID NOS 1-40, respectively, in order of appearance) used for PCR fingerprint verification.

DETAILED DESCRIPTION OF THE PREFERRED EMBODIMENTS

Definitions

Figures 1, 2, 3:
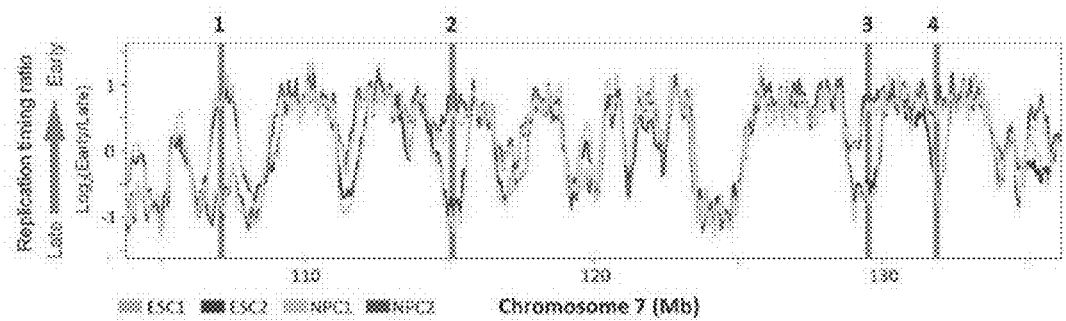
FIG. 1 shows a replication timing fingerprint showing four 200 kb regions in chromosome 7.
FIG. 2 shows the replication timing ratio for each of the four 200 kb regions of FIG. 1.
FIG. 3 shows the total differences in replication timing for all four fingerprinting regions of FIG. 1 between all combinations of the two replicates from these two cell types.

Where the definitions of terms depart from the commonly used meanings of the terms, applicant intends to utilize the definitions provided below, unless specifically indicated.

For purposes of the present invention, it should be noted that the singular forms, "a," "an" and "the," include reference to the plural unless the context as herein presented clearly indicates otherwise.

For purposes of the present invention, a value or property is "based" on or "derived" from a particular value, property, the satisfaction of a condition or other factor if that value is derived by performing a mathematical calculation or logical decision using that value, property or other factor.

For purposes of the present invention, the term "array" and the term "microarray," when used to determine the replication timing profile for a population of cells, refer interchangeably to a field or array of a multitude of spots corresponding to nucleic acid probes or oligonucleotides for all or at least a portion of the genome of a species placed on a support or substrate to allow for simultaneous detection and/or quantification of nucleic acid molecules present in one or more sample(s) by hybridization as commonly understood in the art. For purposes of the present invention, the term "array" generally refers to a genomic array, such as a comparative genomic hybridization (CGH) array, a tiling array, etc.

For purposes of the present invention, the term "cell type" refers to the kind, identity and/or classification of cells according to any and all criteria, such as their tissue and species of origin, their differentiation state, whether or not (and in what manner) they are normal or diseased, etc. For example, the term "cell type" may refer separately and specifically to any specific kind of cell found in nature, such as an embryonic stem cell, a neural precursor cell, a myoblast, a mesodermal cell, etc. Such a list of possible cell types is meant herein to be unlimited.

For purposes of the present invention, the term "computer" refers to any type of computer or other device that implements software, including an individual computer such as a personal computer, laptop computer, tablet computer, mainframe computer, mini-computer, etc. A computer also refers to an electronic devices such as a smartphone, an eBook reader, a cell phone, a television, a handheld electronic game console, a video game console, a compressed audio or video player such as an MP3 player, a Blu-ray player, a DVD player, a microwave oven, etc. In addition, the term "computer" refers to any type of network of computers, such as a network of computers in a business, a computer bank, the Cloud, the Internet, etc. A computer may include a storage device, memory or other hardware and/or software for loading computer programs or other instructions into the computer. A computer may include a communication unit. The communication unit may allow the computer to connect to other databases and the Internet through an I/O interface. The communication unit may allow the transfer to, as well as reception of data from, other databases. The communication unit may include a modem, an Ethernet card or any similar device that enables the computer system to connect to databases and networks such as LAN, MAN, WAN and the Internet. A computer may facilitate inputs from a user through an input device, accessible to the system through the I/O interface. A computer may execute a set of instructions that are stored in one or more storage devices, in order to process input data. The storage devices may also hold data or other information as desired. The storage element may be in the form of an information source or a physical memory element present in the processing machine. The set of instructions may include various commands that instruct the processing machine to perform specific tasks, such as the steps that constitute the method of the present technique. The set of instructions may be in the form of a software program. Further, the software may be in the form of a collection of separate programs, a program module with a larger program or a portion of a program module, as in the present technique. The software may also include modular programming in the form of object-oriented programming. The processing of input data by the processing machine may be in response to user commands, results of previous processing or a request made by another processing machine. In one embodiment of the present invention a computer, may be used to implement steps of the method of the present invention and steps of the various protocols described below.

For purposes of the present invention, the term "differential," the term "replication timing profile differential" and the term "replication timing differential" refer interchangeably to differences in replication timing values between any combination of: (1) one or more replication timing profile(s); (2) a replication timing fingerprint; and/or (3) one or more informative segment(s) of a replication timing fingerprint. For example, the "replication timing differential" may refer to differences in replication timing ratios, such as differences in replication timing ratios expressed on a logarithmic scale, between two or more populations of cells or cell types at a given genomic or chromosomal locus or along the length of at least a segment of one or more chromosome(s) within a genome, etc.

For purposes of the present invention, the term "domain number" refers to an index of a genomic window, and is platform-specific and tied to median probe density. For example, an array with 5.8 kb median probe density would have values averaged in nonoverlapping windows of 35 probes (5.8×35=~200 kb), and an average of the first 35 probes would represent domain number (or region) 1.

For purposes of the present invention, the term "epigenetic signature" and the term "epigenetic signatures" refer broadly to any manifestation or phenotype of cells of a particular cell type that is believed to derive from the chromatin structure of such cells.

For purposes of the present invention, the term "epigenetics," the term "epigenetic markers" and the term "epigenetic parameters" generally refer to chemical modifications of DNA, histones or other chromatin-associated molecules that impart changes in gene expression, such as methylation, acetylation, ubiquitylation, etc. However, the terms "epigenetics," "epigenetic markers" and "epigenetic parameters" may refer more generally to any changes in chromatin structure that affect gene expression apart from DNA sequence. For example, the terms "epigenetics," "epigenetic markers" and "epigenetic parameters" may refer to incorporation of histone variants or chromosomal remodeling by enzymes.

For purposes of the present invention, the term "genome-wide" and the term "whole genome" may refer interchangeably to the entire genome of a cell or population of cells. Alternatively, the terms "genome-wide" or "whole genome" may refer to most or nearly all of the genome. For example, the terms "genome-wide" or "whole genome" may exclude a few portions of the genome that are difficult to sequence, do not differ among cells or cell types, are not represented on a whole genome array, or raise some other issue or difficulty that prompts exclusion of such portions of the genome.

For purposes of the present invention, the term "genomic array" is an array having probes and/or oligonucleotides corresponding to both coding and noncoding intergenic sequences for at least a portion of a genome and may include the whole genome of an organism. For example, a "genomic array" may have probes and/or oligonucleotides for only portions of a genome of an organism that correspond to replication timing fingerprint(s) or informative segments of fingerprint(s). The term "genomic array" may also refer to a set of nucleic acid probes or oligonucleotides representing sequences that are more or less evenly spaced along the length of each chromosome or chromosomal segment. However, even spacing of probes may be dispensable with very high-density genomic arrays (i.e., genomic arrays having an average probe spacing of much less than about 6 kilobases (kb)).

For purposes of the present invention, the term "hardware and/or software" refers to a device that may be implemented by digital software, digital hardware or a combination of both digital hardware and digital software.

For purposes of the present invention, the term "high resolution array" or "high resolution genomic array" generally refers a genomic array having sufficient resolution to provide enough information to generate a smooth replication timing profile to reliably determine the exact positions, lengths, boundaries, etc., of the replication timing domains. The term "high resolution array" or "high resolution genomic array" may correspond to the whole genome or a substantial portion of a genome of a particular cell or population of cells. The term "high resolution array" or "high resolution genomic array" may also refer to a genomic array having an average probe spacing of about 6 kilobases (kb) or less.

For purposes of the present invention, the term "individual" refers to any living organism or part of a living organism such as an organ, tissue, cell, etc.

For purposes of the present invention, the term "informative segment" and the term "informative segments" refer to one or more contiguous portions or segments of one or more chromosome(s) within a genome that are used to define a replication timing fingerprint. In other words, the terms "informative segment" or "informative segments" may refer to one or more contiguous portions or segments of one or more chromosome(s) within a genome that differ between two or more different cell types. For example, the terms "informative segment" or "informative segments" may refer to one or more regions or segments of a genome for a population of cells of a particular cell type having the following characteristics: (1) the region covers at least about 50 kilobases (kb) of genomic DNA; and (2) the region has at least about a 0.5 replication timing ratio differential across such length compared to all other cell types, or at least compared to all other relevant cell types.

For purposes of the present invention, the term "machine-readable medium" refers to any mechanism that stores information in a form accessible by a machine such as a computer, network device, personal digital assistant, manufacturing tool, any device with a set of one or more processors, etc. For example, a machine-readable medium may be a recordable/non-recordable medium (e.g., a read-only memory (ROM), a random access memory (RAM), a magnetic disk storage medium, an optical storage medium, a flash memory device, etc.), a bar code, an RFID tag, etc.

For purposes of the present invention, the term "mammalian cells" refers to a population of cells that are, or were, originally derived from a mammalian organism. The term "mammalian cells" may include primary cells derived from a mammalian species or a cell line originally derived from a mammalian species. The term "mammalian cells" may refer to a homogeneous population of cells from a mammalian organism.

For purposes of the present invention, the term "population of cells" refers to a homogeneous group or population of cells. The term "population of cells" may also include a single cell in culture having the potential to grow and divide into a plurality of homogeneous cells under appropriate culturing conditions.

For purposes of the present invention, the term "primary cell" refers to a cell or cells isolated from a tissue of an organism and placed in culture. The "primary cell" may be derived from any tissue of any organism, such as a mammalian organism. The term "primary cell" generally includes any cell or cells that may be isolated from a tissue of an organism to create a reasonably homogeneous population of cells, such as by first creating single cell suspensions.

For purposes of the present invention, the term "replication timing fingerprint" refers to one or more segments or portions of a replication timing profile for a particular type of cell(s) that differs from all other cell types or all other relevant cell types, which may be used to identify, distinguish, etc., cells of that type. The term "replication timing fingerprint" may refer to the collection of all informative segments of a genome of cells of a particular cell type defined as segments that display a replication timing profile that differs from the replication timing profiles of one or more other cell types. The term "replication timing fingerprint" may further include one or more informative segment(s) that have replication timing profiles that are shared by two or more cell types (i.e., the replication timing profiles are identical or similar) for purposes of comparing a population of cells to a limited set of candidate cell types that have a different replication timing profile for such informative segment(s). A "replication timing fingerprint" may generally exclude uninformative segments that are not consistent among cells of the same type or that do not differ among cells of different types. For purposes of the present invention, the term "replication timing fingerprint" of a cell type refers to a set of genomic regions useful for classification, along with their associated replication timing values.

For purposes of the present invention, the term "replication timing domain" refers to a contiguous region of a chromosome of a cell or population of cells having roughly the same (i.e., early vs. late) replication timing, such as a contiguous region of a chromosome of a cell or population of cells having a roughly equal replication timing ratio value.

For purposes of the present invention, the term "replication timing profile" refers to a series of values for replication timing (e.g., early vs. late S-phase replication timing) along the length of at least a segment of one or more chromosome(s) within a genome. For example, the "replication timing profile" may be expressed as a series of replication timing ratio values, such as early/late S-phase replication or late/early S-phase replication, along the length of at least a segment of one or more chromosome(s), which may further be expressed on a logarithmic scale. Alternatively, the "replication timing profile" may refer to a ratio of the amounts of S-phase DNA to G1-phase DNA from a population of asynchronously dividing cells along the length of at least a segment of one or more chromosome(s), which may further be expressed on a logarithmic scale, with a higher ratio indicating earlier replication and a lower ratio indicating later replication. The term "replication timing profile" may include a replication timing fingerprint for a particular cell type or a set of replication timing profiles for informative segments of a replication timing fingerprint for a particular cell type. The term "replication timing profile" may further include a replication timing profile differential between any combination of: (1) one or more replication timing profile(s); (2) a replication timing fingerprint; and/or (3) one or more informative segment(s) of a replication timing fingerprint(s). The "replication timing profile" may be determined, for example, by quantifying an amount of replicated DNA in a sample from a population of cells by measuring fluorescently labeled DNA, by sequencing, etc.

For purposes of the present invention, the term "replication timing test profile" refers to the replication timing profile for a population of cells of interest having an unknown or uncertain identity to the user of the embodiments of the methods of the present invention.

For purposes of the present invention, the term "replication timing ratio" refers to a ratio value for the timing of replication at a particular locus of a chromosome within the genome of a cell. For example, the "replication timing ratio" may be a ratio of the extent of replication in early S-phase cells divided by the extent of replication in late S-phase cells, or vice versa, at a given locus. Alternatively, the replication timing ratio may be expressed on a logarithmic scale, such as $\log_2$(early/late) or $\log_2$(late/early). Alternatively, for example, the term "replication timing ratio" may refer to the ratio of the extent of replicated DNA in S-phase cells to the amount of DNA in G1-phase cells. The extent of replication or the amount of DNA may be measured, for example, by the fluorescence intensity of an attached label.

For purposes of the present invention, the term "replication timing reference profile" refers to a replication timing profile used as a basis for comparison to identify and/or distinguish a population of cells based on the population's replication timing test profile. Such "replication timing reference profile" may include a replication timing profile for a population of cells, an average replication timing profile for a group of related or identical cells or from replicate experiments, a replication timing fingerprint, one or more informative segment(s) of a replication timing fingerprint, etc., or any combination thereof. Such a "replication timing reference profile" may be simultaneously or previously determined, may be contained in a database, etc.

For purposes of the present invention, the term "resolution," with reference to arrays, refers to how much resolution may be achieved along the length of one or more chromosomes. In general, the more probes and/or oligonucleotides there are along a given length of a chromosome, the greater or higher the resolution may be for such length of a chromosome, assuming roughly equal spacing. Therefore, the terms "density" or "probe density" for an array are directly related to the term "resolution," since a greater or higher probe density along a given length of a chromosome would generally result in greater or higher resolution for the same length of a chromosome. Conversely, the term "spacing" or "probe spacing" is inversely related to gene density and resolution for an array, since a lower or reduced spacing on average between probes and/or oligonucleotides on the array as a function of chromosomal position would generally result in greater or higher resolution or probe density. For example, an array having an average "probe spacing" of about 6 kb or less along a length of a chromosome would have a "probe density" or "resolution" of about 6 kb or higher for such length of chromosome.

For purposes of the present invention, the term "spot" refers to an area, region, etc., of the surface of a support, substrate, etc., having identical, similar and/or related nucleic acid probe or oligonucleotide sequences. Such nucleic acid probes may include vectors, such as BACs, PACs, etc. Each "spot" may be arranged so that it does not touch, become indistinguishable from or become continuous with other adjacent spots.

For purposes of the present invention, the term "storage" and the term "storage medium" refer to any form of storage that may be used to store bits of information. Examples of storage include both volatile and non-volatile memories such as ERAM, flash memory, floppy disks, Zip™ disks, CD-ROM, CD-R, CD-RW, DVD, DVD-R, DVD+R, hard disks, optical disks, etc.

For purposes of the present invention, the term "visual display device" or "visual display apparatus" includes any type of visual display device or apparatus such as a CRT monitor, an LCD screen, an LED screen, a projected display, a printer for printing out an image such as a picture and/or text, a 3D printer, etc. A visual display device may be a part of another device such as a computer monitor, television, projector, cell phone, smartphone, laptop computer, tablet computer, handheld music and/or video player, personal digital assistant (PDA), handheld game player, head-mounted display, heads-up display (HUD), global positioning system (GPS) receiver, automotive navigation system, dashboard, watch, microwave oven, electronic organ, automated teller machine (ATM), etc. A visual display device may be used to display to a user images of the various images, plots, graphs, etc. described below and shown in the drawings. A printer may "display" an image, plot, graph, etc. to a user by printing out the image, plot, graph, etc.

Description

Many types of epigenetic profiling have been used to classify stem cells, stages of cellular differentiation, and cancer subtypes. Existing methods focus on local chromatin features such as DNA methylation and histone modifications that require extensive analysis for genome-wide coverage. Replication timing has emerged as a highly stable cell type-specific epigenetic feature that is regulated at the megabase-level and is easily and comprehensively analyzed genome-wide. In one embodiment, the present invention provides a cell classification method using 67 individual replication timing profiles from 34 mouse and human cell lines and stem cell-derived tissues, including new data for mesendoderm, definitive endoderm, mesoderm and smooth muscle. Using a Monte Carlo approach for selecting features of replication timing profiles conserved in each cell type, "replication timing fingerprints" unique to each cell type are identified and a k nearest neighbor approach is applied to predict known and unknown cell types. This method of the present invention has been used to correctly classify 67/67 independent replication-timing profiles, including those derived from closely related intermediate stages. This method of the present invention may also be used to derive fingerprints for pluripotency in human and mouse cells.

Interestingly, the mouse pluripotency fingerprint overlaps almost completely with previously identified genomic segments that switch from early to late replication as pluripotency is lost. Thereafter, replication timing and transcription within these regions become difficult to reprogram back to pluripotency, suggesting these regions highlight an epigenetic barrier to reprogramming. In addition, the major histone cluster Hist1 consistently becomes later replicating in committed cell types, and several histone H1 genes in this cluster are downregulated during differentiation, suggesting a possible instrument for the chromatin compaction observed during differentiation. According to one embodiment of the present invention, unknown samples may be classified independently using site-specific PCR against fingerprint regions.

In sum, replication timing fingerprints provide a comprehensive means for cell characterization and are a promising tool for identifying regions with cell type-specific organization.

While continued advances in stem cell and cancer biology have uncovered a growing list of clinical applications for stem cell technology, errors in identifying cell lines have undermined a number of recent studies, highlighting a growing need for improvements in cell typing methods for both basic biological and clinical applications of stem cells. Induced pluripotent stem cells (iPSCs)—adult cells reprogrammed to a pluripotent state—show great promise for patient-specific stem cell treatments, but more efficient derivation of iPSCs depends on a more comprehensive understanding of pluripotency. In one embodiment, the present invention provides a method to identify sets of regions that replicate at unique times in any given cell type (replication timing fingerprints) using pluripotent stem cells as an example, and show that genes in the pluripotency fingerprint belong to a class previously shown to be resistant to reprogramming in iPSCs, identifying potential new target genes for more efficient iPSC production. In one embodiment of the present invention, the order in which DNA is replicated (replication timing) provides a novel means for classifying cell types, and can reveal cell type-specific features of genome organization.

In mammals, replication of the genome occurs in large, coordinately firing regions called replication domains [1-7]. These domains are typically one to several megabases, roughly align to genomic features such as isochores, and are closely tied to subnuclear position, with transitions to the nuclear interior often coupled to earlier replication, and transitions to the periphery to later replication [4,5,8,9]. Given their connections to subnuclear position and remarkably strong correlation to chromatin interaction maps [3], replication timing profiles provide a window into large-scale genome organization changes important for establishing cellular identity. The organization of replication domains is cell type-specific, and a larger number of smaller replication domains is a property of embryonic stem cells (ESCs) [3-5]. Importantly, in both humans and mice, induced pluripotent stem cells (iPSCs) reprogrammed from fibroblasts display a timing profile almost indistinguishable from ESCs, suggesting that replication timing profiles may also be used to measure cellular potency [3,5].

While a wide range of cell classification methods are actively used, the most common practice for verifying identity is to monitor a handful of molecular markers, some of which are shared with other cell types. Genome-wide classification of features such as DNA methylation [10-12], transcription [13,14] and histone modifications [15,16] have in principle more potential to accurately distinguish specific cell types. However, these features of chromatin are highly dynamic at any given genomic site [17], and most measurements require high-resolution arrays and costly antibodies. Moreover, recent reports highlight the unstable nature of transcription and related epigenetic marks in multiple embryonic stem cell lines [18,19]. By contrast, since replication is regulated at the level of large domains, replication timing profiles are considerably less complex to generate and interpret than other molecular profiles. Timing changes occurring during differentiation are on the order of several hundred kilobases and are highly reproducible between various stem cell lines [3-5]. They are also robust to changes in individual chromatin modifications, retaining their normal developmental pattern in G9a(2/2) cells despite strong upregulation of G9a target genes and near-complete loss of H3K9me2 [8].

According to one embodiment, the present invention provides a method for classifying cell types—replication timing fingerprinting—based on genome-wide replication timing patterns in mouse and human ESCs and other cell types. This method was applied to 67 (36 mouse and 31 human) whole-genome replication timing datasets to demonstrate the feasibility of classifying cell types using a minimal set of cell type-specific regions. After identification, these regions were used to classify two independent samples using site-specific PCR. Experimental results, described below, demonstrate that loss of pluripotency is accompanied by consistent changes in replication timing, implicating the replication program as an important factor in maintaining pluripotency and revealing a novel fingerprint for pluripotent stem cells.

Results

Generation of Replication Timing Profiles

In addition to previously reported replication timing profiles. BG02 hESCs were differentiated to mesendoderm and definitive endoderm as previously described [20], as well as ISL+ mesoderm and smooth muscle cultured in defined medium (see Methods section below), and profiled for replication. Replication timing profiles were generated as described previously [3-5,21]. In brief, nascent DNA fractions were collected in early and late S-phase, differentially labeled, and co-hybridized to a whole-genome CGH microarray. The ratio of early and late fraction abundance for each probe—"replication timing ratio"—represents its relative time of replication. Values from individual probes are then smoothed using LOESS (a locally weighted smoothing function) and plotted on log scale (FIG. 1). Replication timing profiles generated in this way are freely available to view or download [22], and those analyzed in this report are summarized in Tables 1 and 2 of FIG. 4.

Generation of Replication Timing Fingerprints

FIGS. 1, 2 and 3 illustrate the basic concept of replication timing fingerprinting. Two exemplary profiles each for D3 embryonic stem cells (ESC1 and ESC2; lighter and darker, respectively) and D3 ESC-derived neural precursor cells (NPC1 and NPC2; lighter and darker, respectively) are overlaid. Given that most of the genome is conserved in replication timing between any two cell types (e.g., 80% conserved between ESCs and NPCs [4]), the first challenge is to choose genomic regions that are differentially replicated within a set of cell types. For purposes of the present invention, the term a "replication timing fingerprint" of a cell type refers to a set of genomic regions useful for classification, along with their associated replication timing values. For a simplified example, FIG. 1 shows exemplary fingerprint regions for a segment of chromosome 7 (FIG. 1, gray bars 1, 2, 3 and 4). Note that the four regions change dramatically upon differentiation to neural precursors (e.g., ESC2 vs. NPC1; FIGS. 1 and 2), but have replication timing values that are well conserved between replicate experiments (e.g., ESC1 vs. ESC2). Similarly widespread changes in replication timing profiles between any two different cell types profiled have been observed [1,3-5,7].

FIGS. 1, 2 and 3 show a simplified replication timing fingerprint. FIG. 1 shows four 200 kb regions in chromosome 7, highlighted in grey, selected for a simplified fingerprint using two replicates each of ESCs (on replicate shown with a lighter line, one replicate shown with a darker line) and NPCs (on replicate shown with a lighter line, one replicate shown with a darker line). FIG. 2 shows the replication timing ratio for each region in each experiment, with the total distances in replication timing for all fingerprinting regions between replicates of ESCs or NPCs in grey. Note that distances between the two different cell types (ESC vs. NPC) are substantially higher than those between replicate profiles (e.g., 6.1 for ESC2 vs. NPC1; shown between the grey boxes). FIG. 3 shows the total differences in replication timing for all four fingerprinting regions between all combinations of the two replicates from these two cell types. Highlighted in grey are the values for the two replicates of each cell type, which are considerably less than the values for any of the inter-cell type comparisons. Shown below the table of FIG. 3 is the "distance ratio," calculated as the average distance between cell types (or between replicates) divided by the average distance within cell types. The distance ratio represents the degree of separation between replication timing profiles in regions used for classification.

As classification methods require a measure of distance between samples, in the method according to one embodiment of the present invention, the "distance" between replication timing profiles is defined as the sum of absolute differences in replication timing in fingerprinting regions (FIG. 2). To select an optimal set of fingerprinting regions, in one embodiment of the present invention, a "distance ratio" representing the ratio of the average distance between unlike cell types to the average distance between equivalent cell types is maximized (FIG. 3). This ratio is maximized by selecting regions that are consistently different in replication timing between different cell types but consistently similar between equivalent types. Importantly, the assignment of unlike vs. equivalent cell types is user-defined and flexible, allowing selection of features that best distinguish any group of cells from any other, such as ESCs from NPCs, normal from disease-related cells, or pluripotent from committed cells.

While FIGS. 1, 2 and 3 show a simplified example of four regions distinguishing ESCs from NPCs, real-world classification requires the ability to make distinctions genome-wide between many cell types, making manual selection of regions impractical. Therefore, to make the method generally applicable, an automated algorithm is used in one embodiment of the present invention that is based on Monte Carlo sampling [23] to select regions that best distinguish between all available cell types in genome-wide replication datasets. Alternative approaches evaluated for feature selection and classification included Bayesian networks, nearest neighbor methods, decision trees and SVMs, which were comparably successful only for smaller collections of cell types. Distances between cell types in the method described have been explicitly maximized here in anticipation of translating cell classification to more convenient empirical assays with a limited number of features, because larger timing differences are easier to verify empirically and are more robust to experimental and biological variation.

Monte Carlo Optimization of Fingerprint Regions

Figures 5, 6:
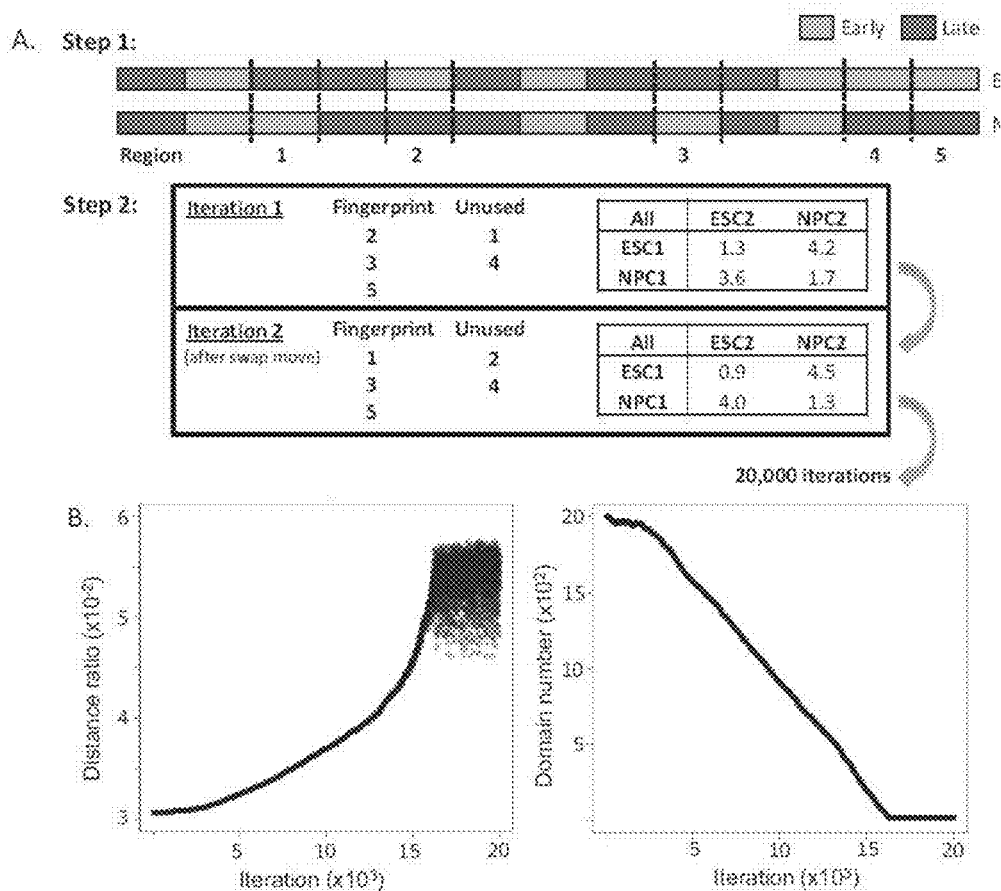
FIG. 5 is a table showing classification errors using a whole genome nearest neighbor approach.
FIG. 6 is a diagram illustrating a Monte Carlo optimization algorithm according to one embodiment of the present invention.

In practice, replication timing fingerprinting is a feature selection problem. Although most genome-wide approaches are both simple and comprehensive, it has been found that genome-wide correlations and distances, while a good first approximation of the relatedness between cell types, are not ideal for classification as the small amount of noise in regions with conserved replication timing is compounded over this relatively large fraction of the genome (FIG. 5). It is therefore desirable to exclude domains that are noisy (having high technical or biological variability), irrelevant (conserved in all cell types) or redundant (containing overlapping information). To achieve this, regions with conserved replication timing between cell types are removed first, resulting in a set of informative regions that can be further optimized by a Monte Carlo selection algorithm.

FIG. 5 is a table showing classification errors using a whole genome nearest neighbor approach. The distances were calculated between profiles as in FIG. 19, using the entire genome rather than an optimized set of fingerprinting regions. Classification errors (indicated by arrow 512) result when distances between cell types are smaller than the distance within cell types. Here, TT2 ESC replicate 1 could be misclassified as an NPC, or D3 NPC replicate 2 as an ESC.

FIG. 6 depicts the Monte Carlo algorithm. To reduce noise from individual probe measurements, replication timing profiles are first averaged into nonoverlapping windows of approximately 200 kb. In one embodiment, the nonoverlapping window size may be from 100 kb to 400 kb in size. In one embodiment of the present invention, the nonoverlapping window size may be from 150 kb to 250 kb in size. In one embodiment of the present invention, the nonoverlapping window size may be from 180 kb to 220 kb in size.

This window size represents a balance between sizes of the regions that change replication timing during development (400-800 kb), and the number of probes needed for timing changes to be deemed statistically significant (35-180 probes are contained in each window depending on the probe density of the array platform; see Methods section below and Table 3 of FIG. 7). An initial set of regions with the highest replication timing changes in the set of replication timing profiles are chosen (a set of chosen regions) to exclude regions with conserved replication timing, and half of these starting regions are randomly selected (a set of selected regions) to calculate initial distances between cell types. The starting regions that are not selected form a set of unused regions. At each iteration of the algorithm, a region can be added to the set of fingerprint regions, removed from the set of fingerprint regions or swapped with an unused region. Using a Metropolis-Hastings criterion [23,24], moves that improve the overall distance ratio are accepted with higher probability than those that do not; after 20,000 or more such moves, a final set of fingerprinting regions is selected.

FIG. 6 is a diagram illustrating a Monte Carlo optimization algorithm according to one embodiment of the present invention. Part A of FIG. 6 shows regions used in replication timing fingerprints is selected using a two step algorithm. First, 200 kb segments with significant changes in replication timing between any two cell types are isolated (chosen to form a set of chosen regions). Next, a random set of these segments is sampled (selected to form a set of selected regions; the remaining chosen regions that are not selected form a set of unused regions) to calculate a distance ratio (FIG. 3) representing the starting separation between cell types, and an iterative algorithm randomly selects between one of three moves: (1) include an unused region in the fingerprint (set of selected regions), (2) remove a region from the fingerprint (set of selected regions) and add the removed region to set of unused regions or (3) swap regions between fingerprint (set of selected regions) and set of unused regions. By the Metropolis-Hastings criterion, moves that improve the separation between cell types (increase the distance ratio criterion) are accepted with a higher probability than those that do not. Part B of FIG. 6 shows the maximization of the distance ratio (left) as domain number (right) decreases to a predetermined minimum (here, n=20).

Table 3 of FIG. 7 provides a summary of algorithm performance using window sizes of 50 kb, 100 kb, 200 kb, and 400 kb. Windows of 200 kb were used for the remaining analyses to correspond with the unit size of developmental replication timing changes, which is typically 400-800 kb [3-5].

Figure 20:
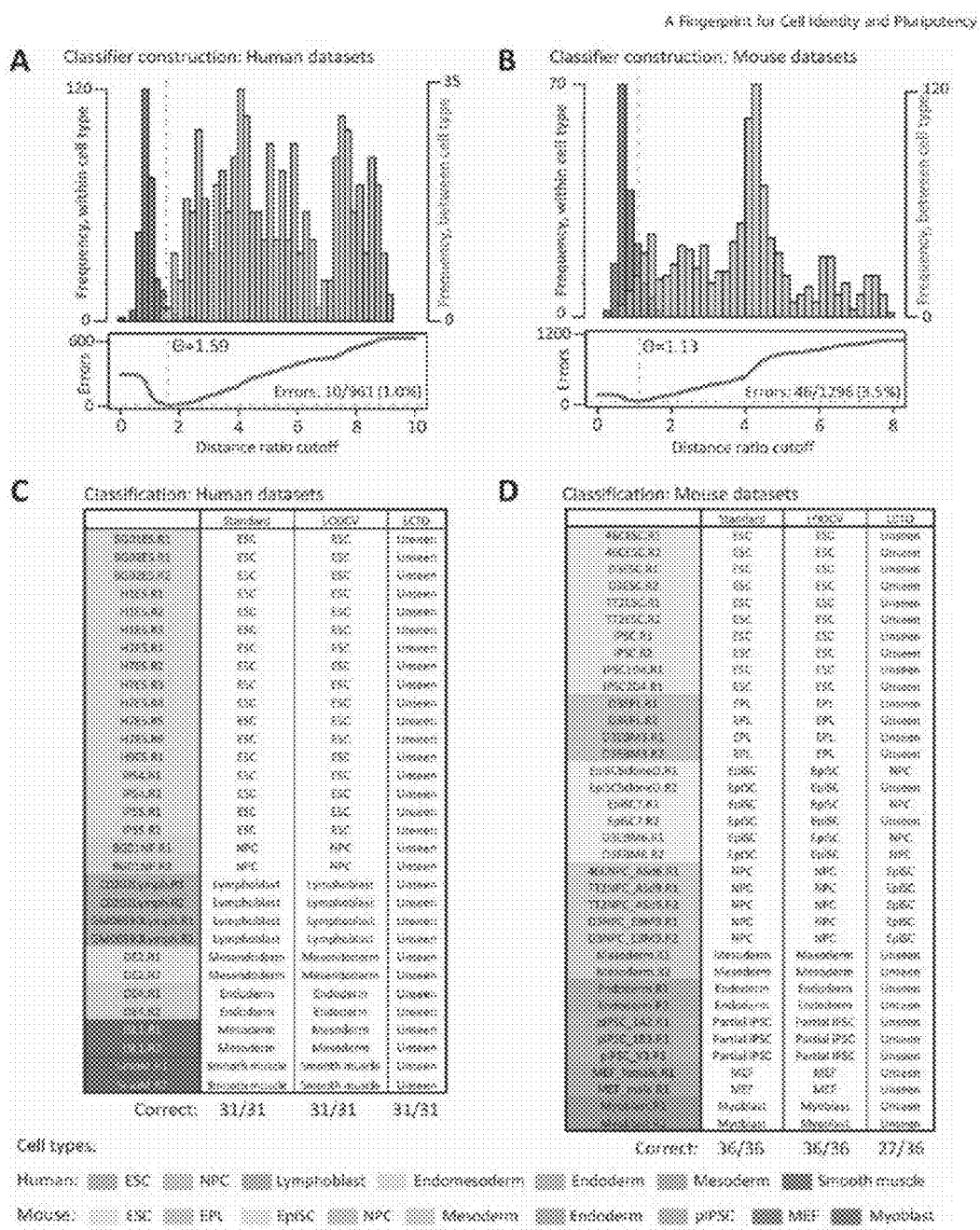
FIG. 20 shows cell type classification using Monte Carlo-selected domains.

As depicted in FIG. 2, the fingerprinting algorithm selects domains with large and reproducible replication timing differences between cell types, discarding those with minimal or variable changes. Before selecting optimal regions (Table A and Graph C of FIG. 2), the average distances between "like"' and "unlike" cell types are similar, translating into classification errors for randomly selected domains (Graph C of FIG. 2) as well as the whole genome (FIG. 5, indicated by arrows 512 and 514). After selection, the separation in distances between like and unlike types becomes very distinct (Table B and Graph D of FIG. 2), even for closely related cell types (FIG. 20). These regions similarly highlight distinctions between cell types both in correlations (FIGS. 8, 9, 10, 11, 12 and 13), and distance matrices between cell types (FIGS. 14, 15, 16 and 17).

Figure 8:
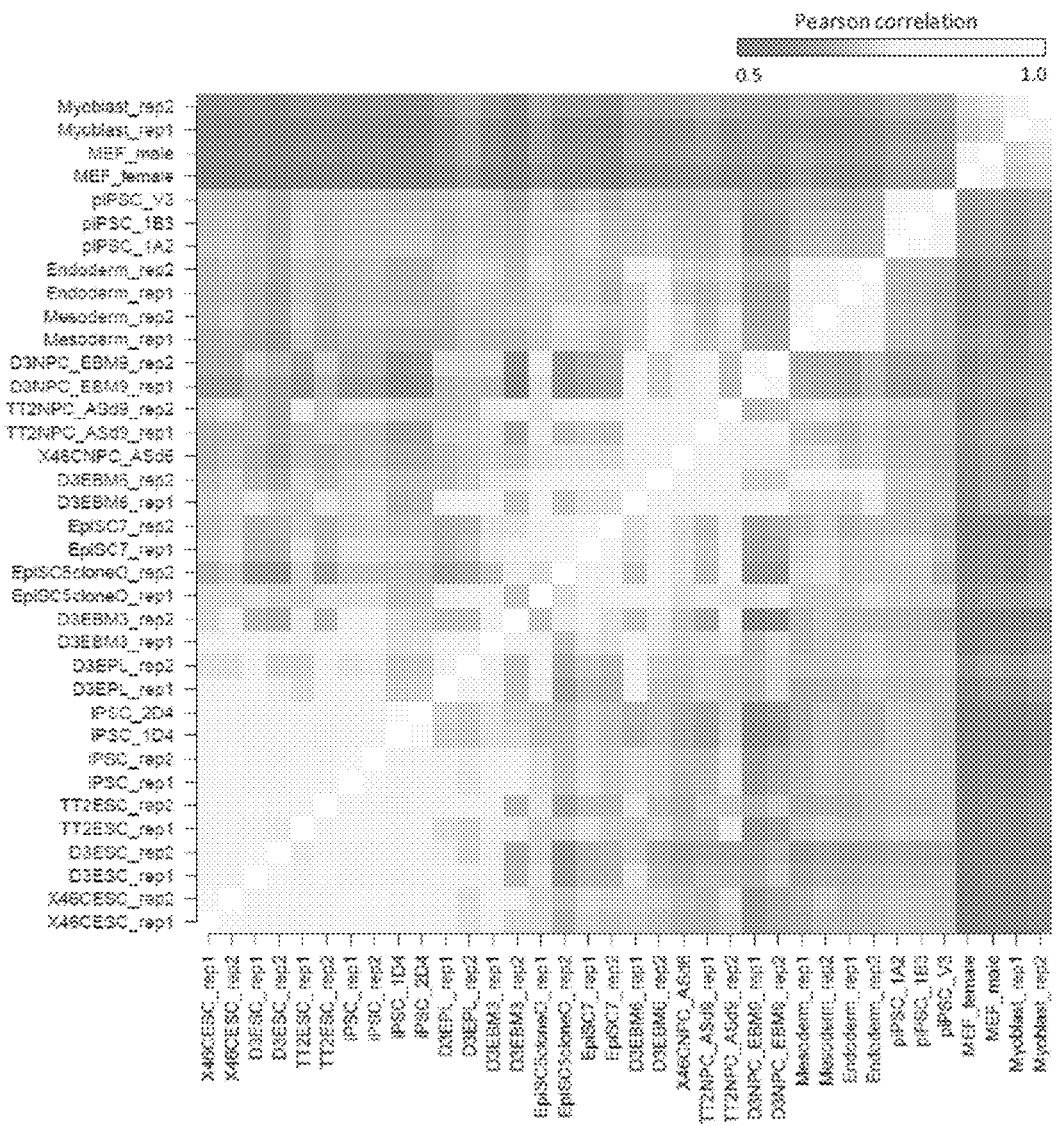
FIG. 8 shows genome-wide correlations between mouse timing datasets.

FIG. 8 shows a genome-wide correlations between mouse timing datasets. Heatmaps depict the level of correlation between timing datasets averaged in 200 kb windows, from low (dark) to high (white). Note the relatively high level of variation in correlations between similar and divergent cell types (compare to FIG. 9).

Figure 9:
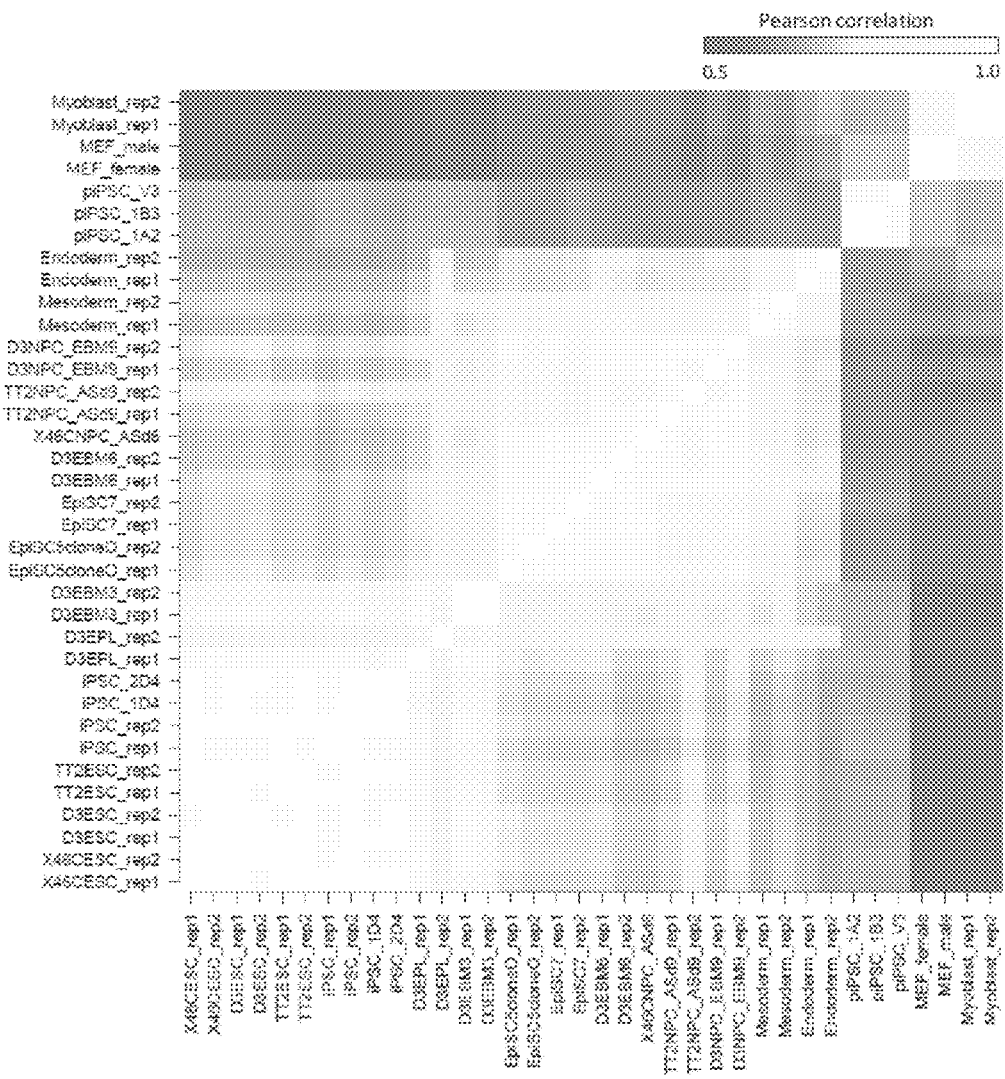
FIG. 9 shows correlations between mouse timing datasets in consensus cell type fingerprint regions.

FIG. 9 shows correlations between mouse timing datasets in consensus cell type fingerprint regions. Heatmaps depict the level of correlation between timing datasets in 200 kb fingerprint regions from low (dark) to high (white). Compare with FIG. 8.

Figure 10:
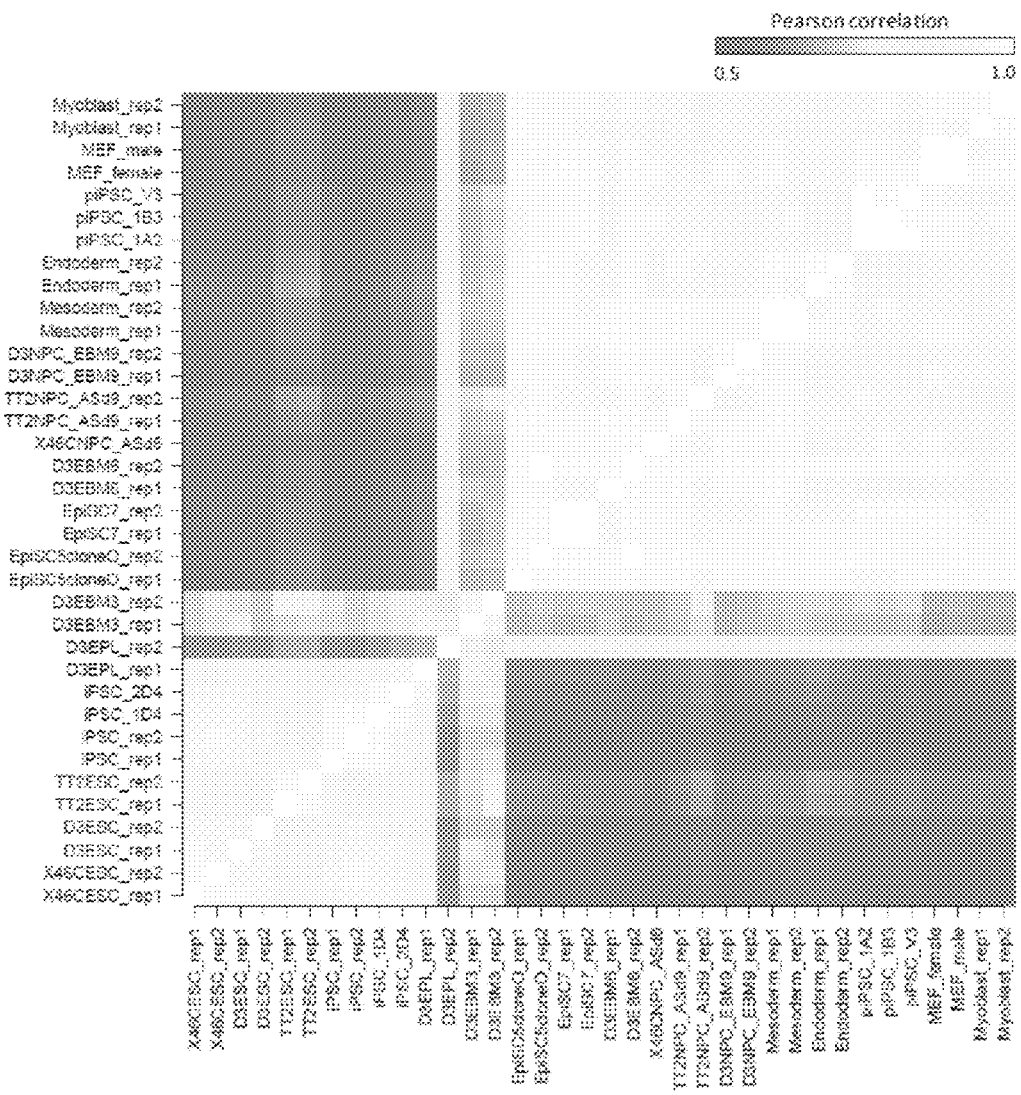
FIG. 10 shows correlations between mouse timing datasets in consensus pluripotency fingerprint regions.

FIG. 10 shows correlations between mouse timing datasets in consensus pluripotency fingerprint regions. Heatmaps depict the level of correlation between timing datasets in 200 kb fingerprint regions, from low (dark) to high (white).

Figure 11:
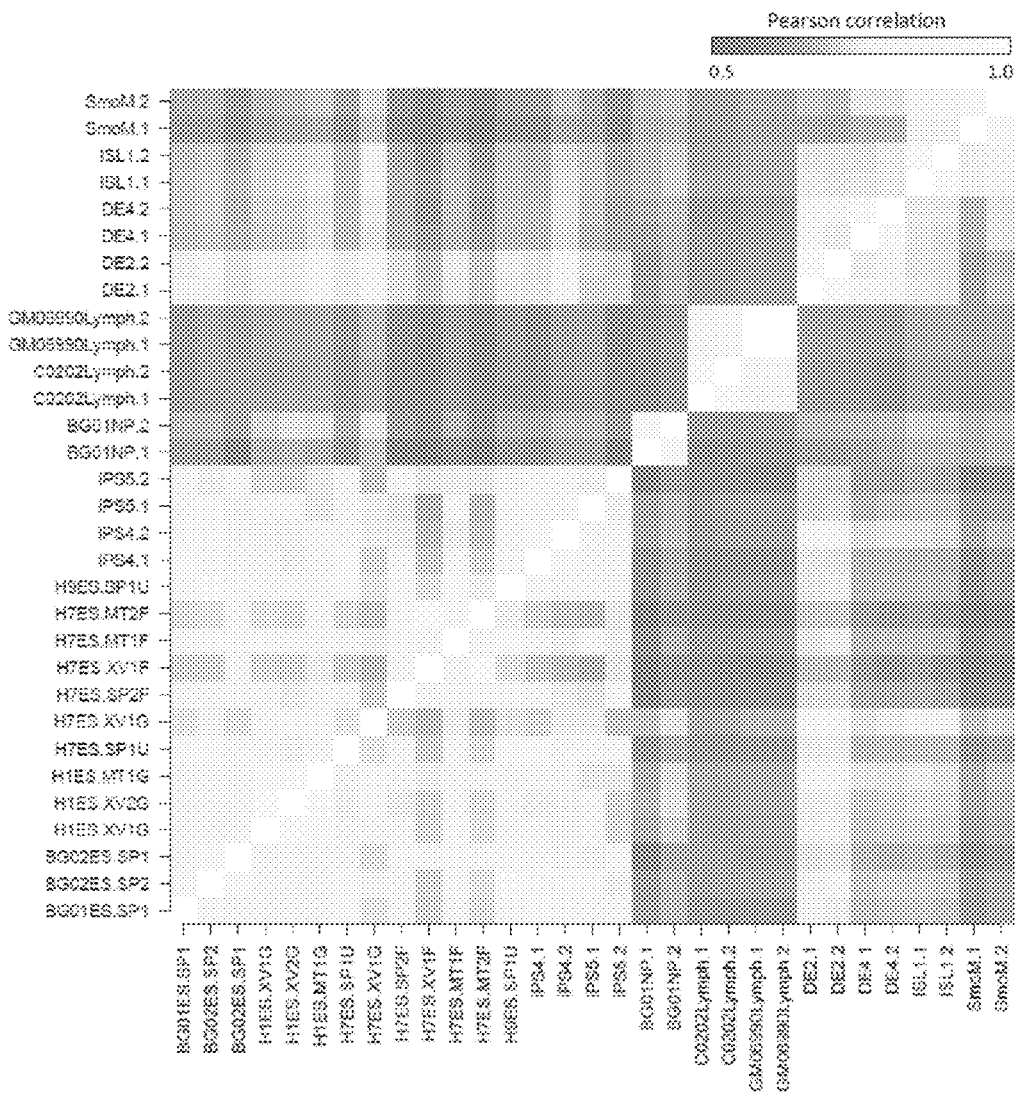
FIG. 11 shows genome-wide correlations between human timing datasets.

FIG. 11 shows genome-wide correlations between human timing datasets. Heatmaps depict the level of correlation between timing datasets averaged in 200 kb windows, from low (dark) to high (white). Note the relatively high level of variation in correlations between similar and divergent cell types (compare to FIG. 12).

Figure 12:
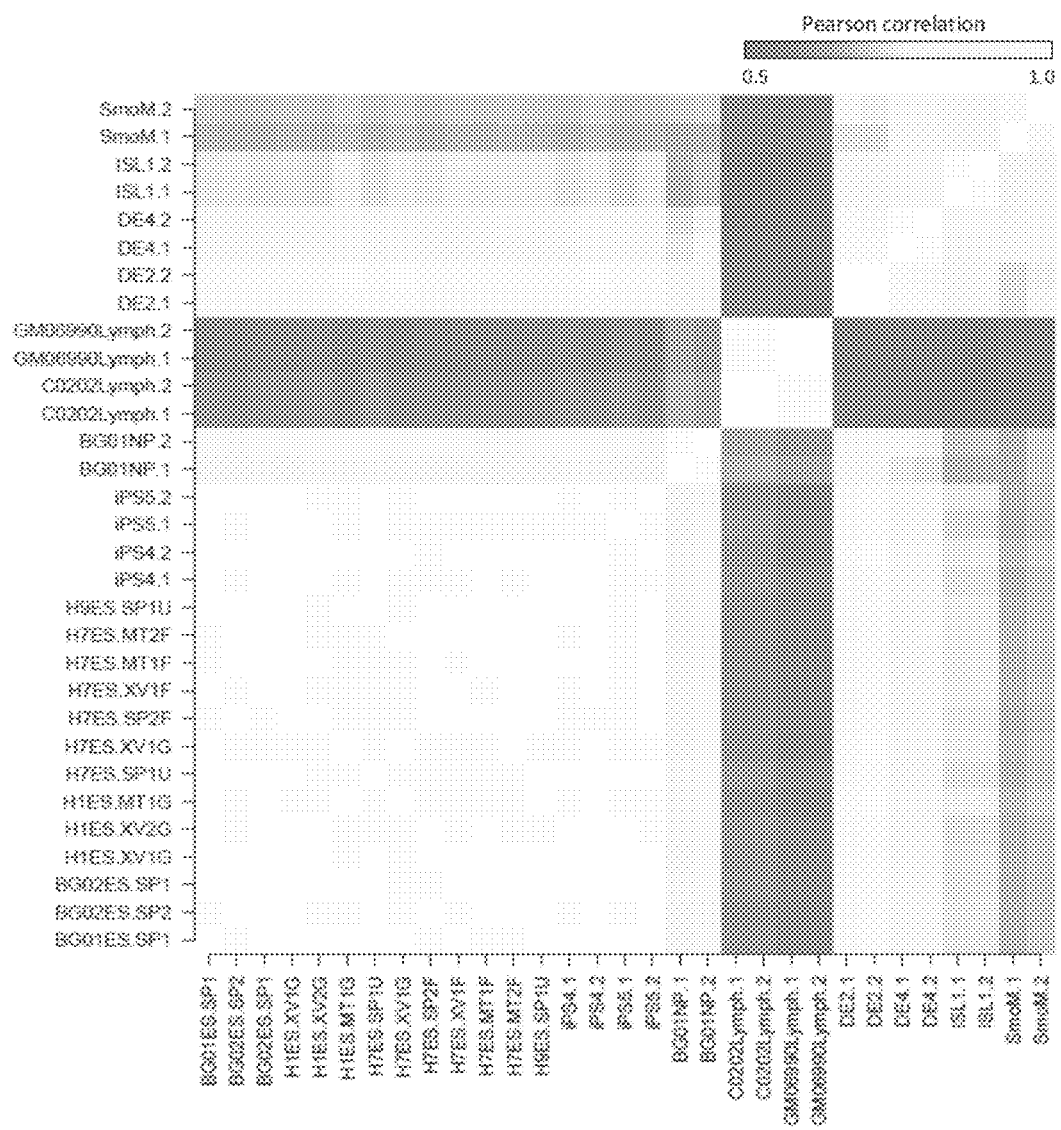
FIG. 12 shows correlations between human timing datasets in consensus cell type fingerprint regions.

FIG. 12 shows correlations between human timing datasets in consensus cell type fingerprint regions. Heatmaps depict the level of correlation between timing datasets in 200 kb fingerprint regions, from low (dark) to high (white).

Figure 13:
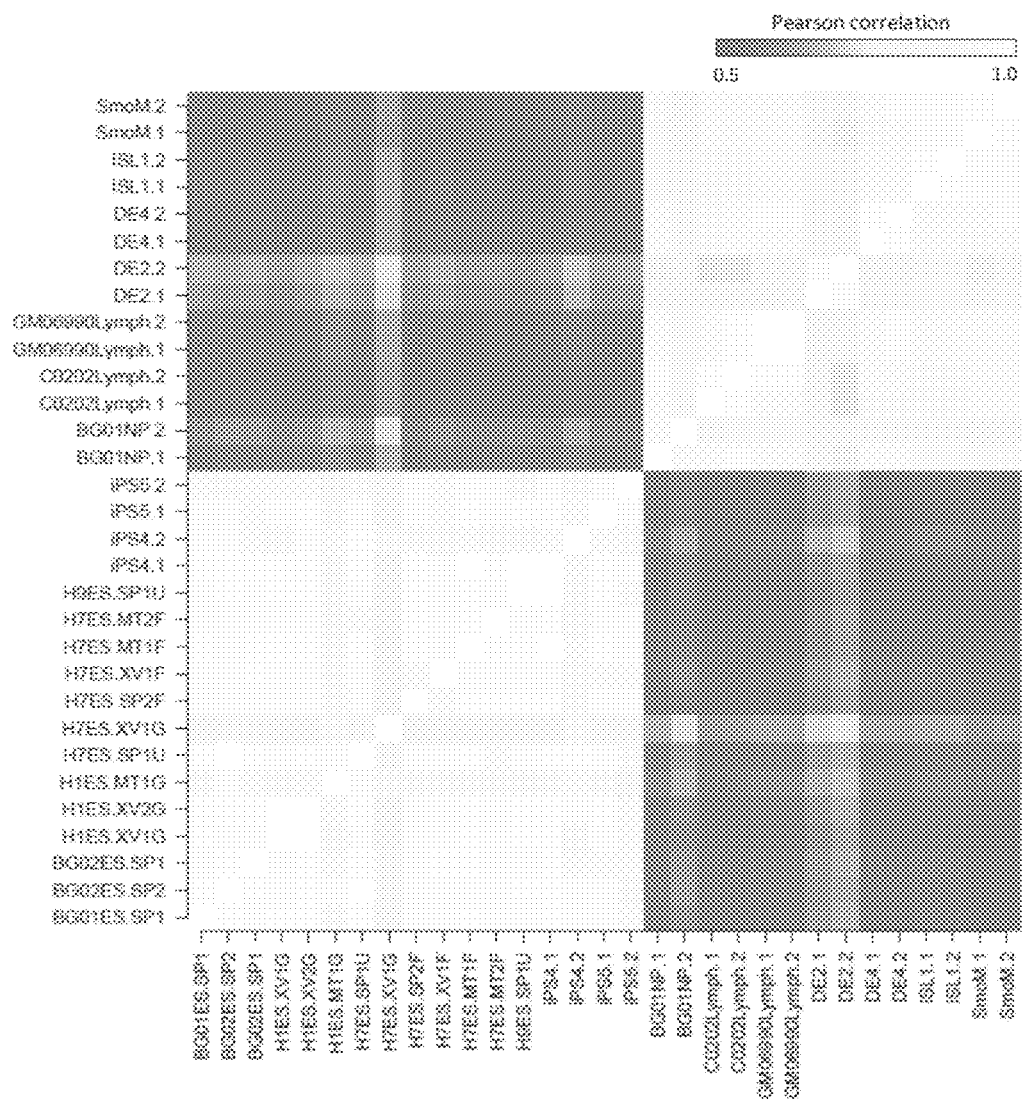
FIG. 13 shows correlations between human timing datasets in consensus pluripotency fingerprint regions.

FIG. 13 shows correlations between human timing datasets in consensus pluripotency fingerprint regions. Heatmaps depict the level of correlation between timing datasets in 200 kb fingerprint regions, from low (dark) to high (white).

Figure 14:
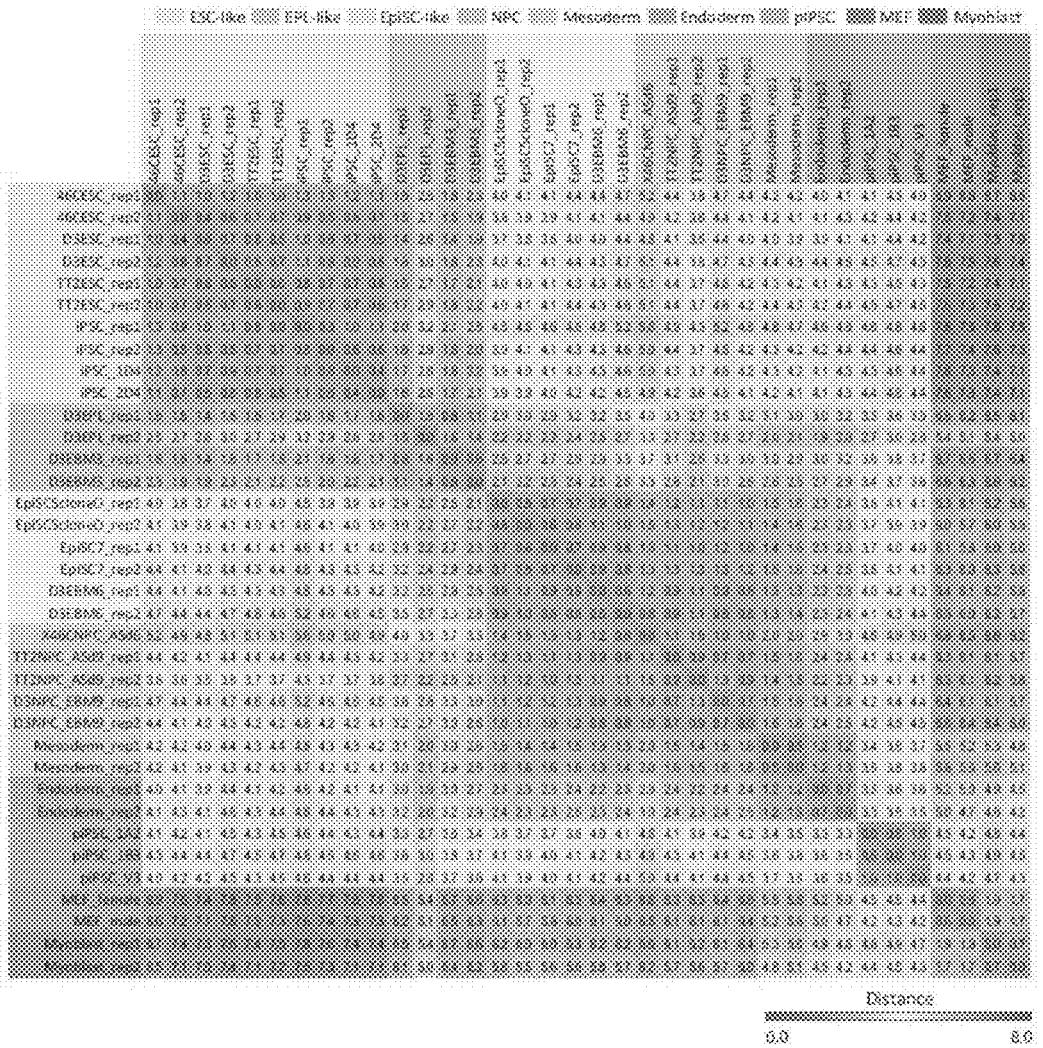
FIG. 14 shows a distance matrix for mouse cell type consensus fingerprint.

FIG. 14 shows a distance matrix for mouse cell type consensus fingerprint. Numbers indicate the Euclidean distance between replication timing profiles measured in the 18 regions included in over 75% of runs of the fingerprinting algorithm. Cell type definitions used for training are indicated by the color map in rows and columns (see color key at top). Color scale for distances relates the relative similarity of cell types in fingerprint regions, from highly similar (0.0) to highly divergent (8.0).

Figure 15:
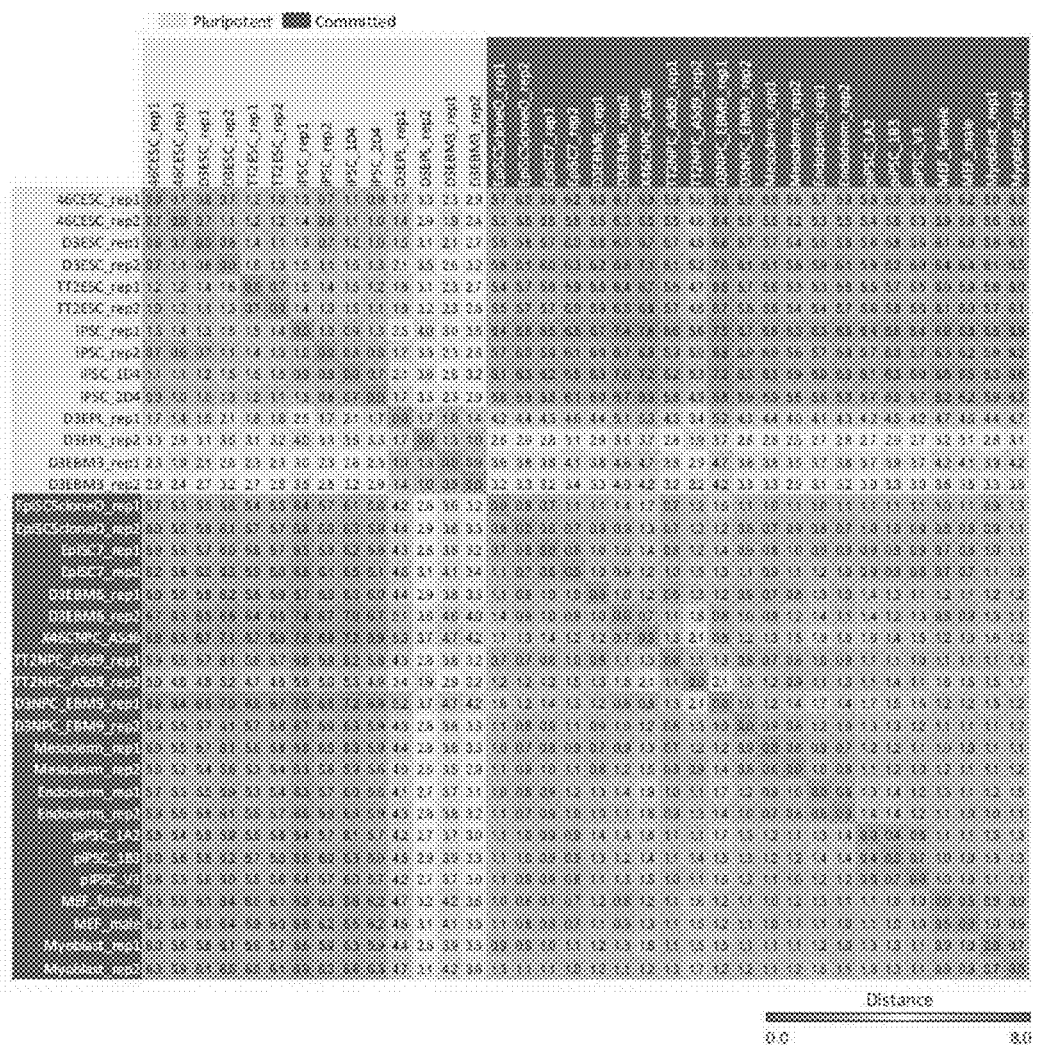
FIG. 15 shows a distance matrix for mouse pluripotency consensus fingerprint.

FIG. 15 shows a distance matrix for mouse pluripotency consensus fingerprint. Numbers indicate the Euclidean distance between replication timing profiles measured in the 18 regions included in over 75% of runs of the fingerprinting algorithm. Cell type definitions used for training are indicated by the color map in rows and columns (lighter: pluripotent cell types; darker: committed cell types) Color scale for numbers relates the relative similarity of cell types in fingerprint regions, from highly similar (0.0) to highly divergent (8.0).

Figure 16:
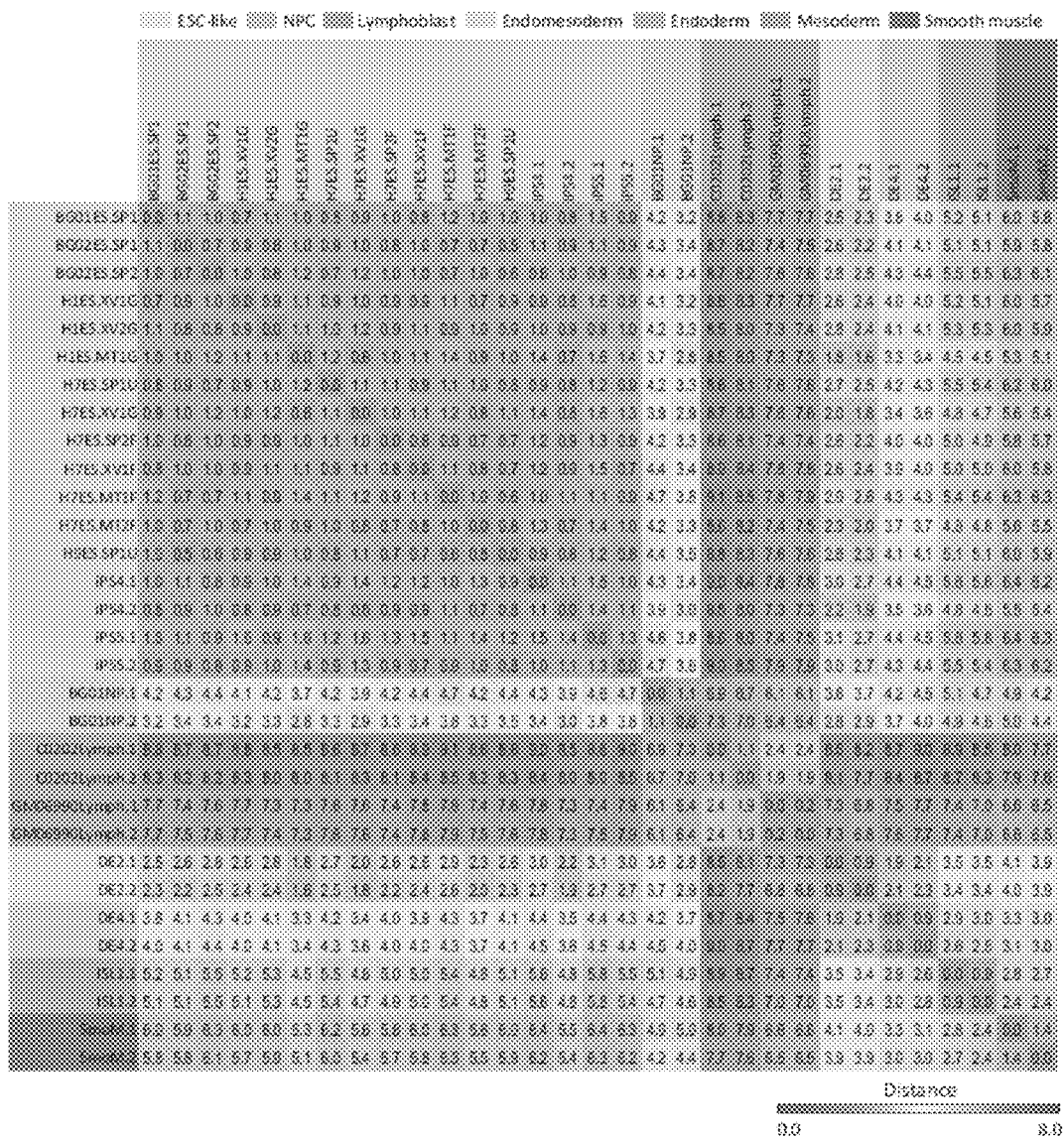
FIG. 16 shows a distance matrix for human cell type consensus fingerprint.

FIG. 16 shows a distance matrix for mouse pluripotency consensus fingerprint. Numbers indicate the Euclidean distance between replication timing profiles measured in the 18 regions included in over 75% of runs of the fingerprinting algorithm. Cell type definitions used for training are indicated by the color map in rows and columns (light blue: pluripotent cell types; dark blue: committed cell types). Color scale for numbers relates the relative similarity of cell types in fingerprint regions, from highly similar (0.0) to highly divergent (8.0).

Figure 17:
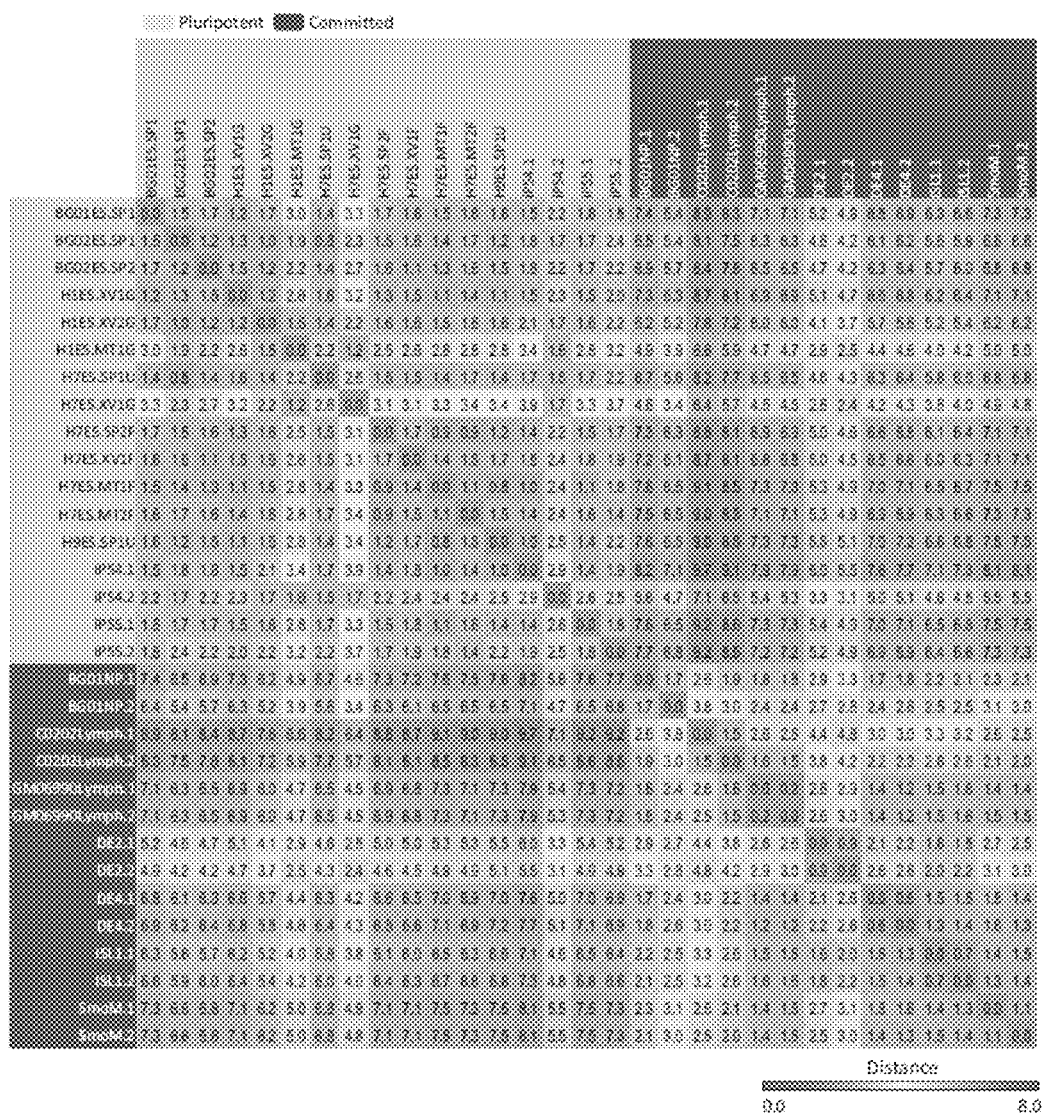
FIG. 17 shows a distance matrix for human pluripotency consensus fingerprint.

FIG. 17 shows a distance matrix for human pluripotency consensus fingerprint. Numbers indicate the Euclidean distance between replication timing profiles measured in the 18 regions included in over 75% of runs of the fingerprinting algorithm. Cell type definitions used for training are indicated by the color map in rows and columns (lighter: plurinotent cell types; darker: committed cell types). Color scale for numbers relates the relative similarity of cell types in fingerprint regions, from highly similar (0.0) to highly divergent (8.0).

Figure 18:
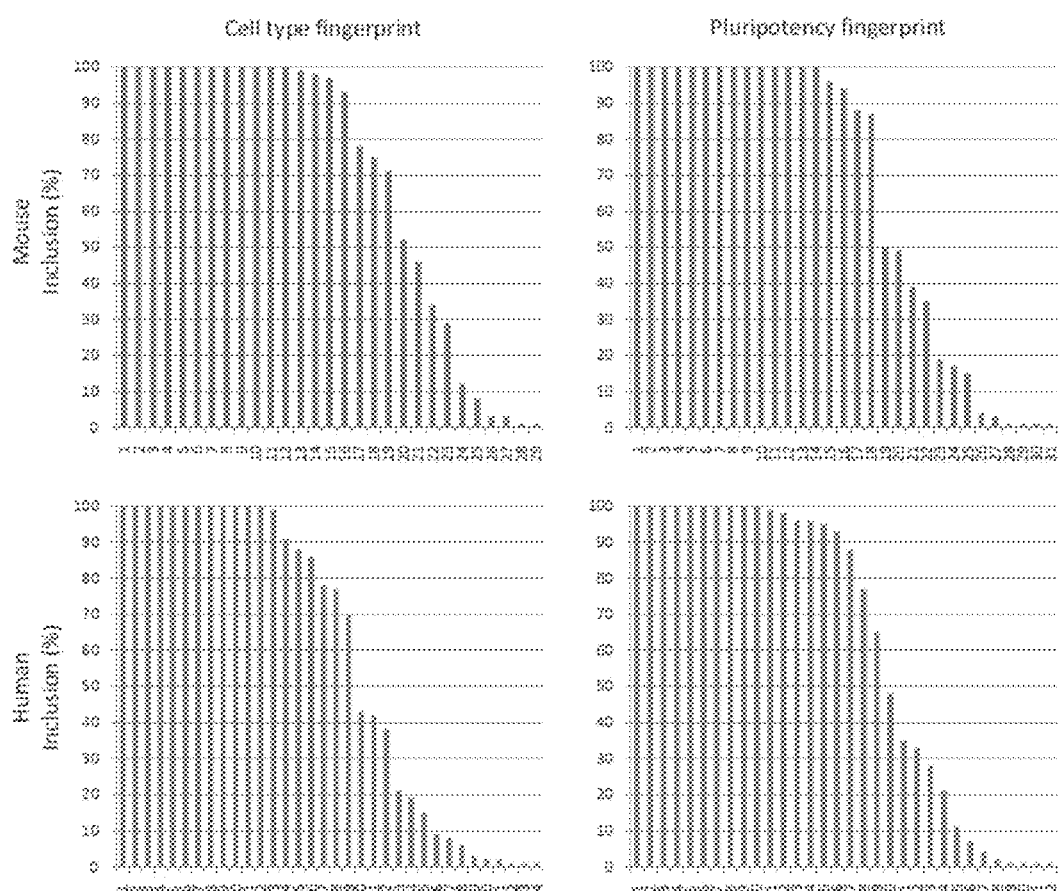
FIG. 18 provides four graphs that show the calculation of consensus fingerprint regions.

Since Monte Carlo selection is stochastic, different sets of fingerprinting regions can be selected in different runs. To evaluate the stability of regions included in replication timing fingerprints, the algorithm is applied 100 times for each type of human and mouse fingerprint constructed (FIG. 18). FIG. 18 shows the calculation of consensus fingerprint regions. Since the Monte Carlo algorithm will randomly include or exclude regions in each run, the suitability of a set of regions for classification can be evaluated by running the algorithm multiple times and choosing the regions most often present. Regions with particularly unique timing in each cell type are often selected in 100/100 trials; here, regions are selected that are included in at least 75 out of 100 runs for "consensus" fingerprints for mouse and human cell type and pluripotency regions. The x-axis for each graph depicts the rank of each region in percentage of runs with that region included.

Results demonstrate that fingerprinting regions are well conserved among multiple rounds of selection, with the top 10-14 regions selected in 100/100 trials in each case. For all subsequent classification, regions used included in at least 75/100 fingerprinting runs. As the distances between profiles derive from either the same or different cell types (Graph C of FIG. 19), their distributions can be used to create a general classifier (Graphs C and D of FIG. 19 and Chart A of FIG. 20), with an error rate proportional to the overlap in distances shared by "like" and "unlike" cell type comparisons (Graphs C and D of FIG. 19, indicated by arrow 1912). This allows us to state a level of confidence for a given prediction, as well as estimate the similarity of a cell type to others. To refine this classification, the k-nearest-neighbor rule [25](kNN; k=3) is applied to assign cell types according to the three most similar profiles in the training set. Distances below the threshold—h=2.4 in Graph D of FIG. 19—are hypothesized to derive from similar cell types, and are used with kNN to classify profiles according to the closest profiles in the training set. Distances above the threshold are presumed to derive from different cell types, preventing kNN from classifying highly divergent RT profiles as the cell type of the most similar known profile.

Figure 19:
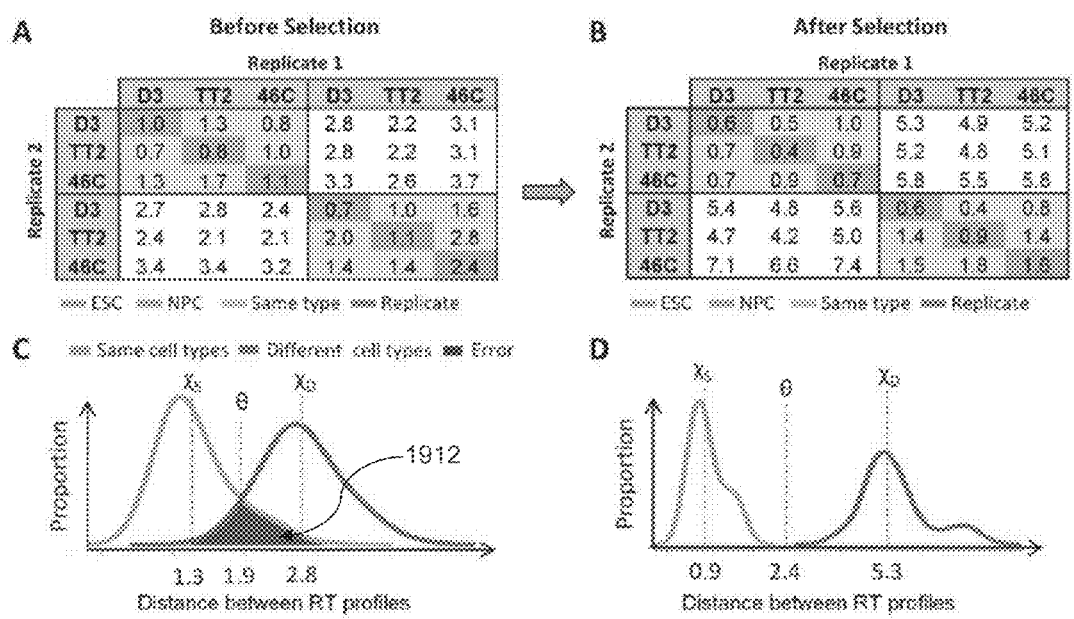
FIG. 19 shows a Monte Carlo optimization of fingerprinting regions.

FIG. 19 shows a Monte Carlo optimization of fingerprinting regions. A Monte Carlo algorithm is used to select regions with maximal differences in replication timing between cell types and minimal differences between replicates to obtain an optimized set of genomic regions for classification using the nearest-neighbor method. Tables A and B of FIG. 19 show how the selection of fingerprinting regions accentuates differences between cell types while diminishing those within equivalent cell types (light gray) and replicates (dark gray). To calculate confidence levels of predictions the distributions of distances within (grey; lighter line) and between (darker line) cell types are used, shown here for 30 runs before and after selection in graphs C and D, respectively. The error rate of prediction is represented by the shaded area, indicated by arrow 1912, shared by comparisons between similar or distinct cell types, with average distances of xS and xD respectively. The optimal classifier, h, is estimated by minimizing the number of misclassified distances as in FIGS. 20 and 21. Above this distance, datasets are predicted to originate from different cell types.

Classification of Cell Types Using Fingerprint Regions

To test the ability of the method according to one embodiment of the present invention to select suitable regions for classification, the method is applied to predict the known identity of 9 mouse and 7 human cell types with 36 and 31 total experimental replicates, respectively. Datasets used for prediction are summarized in Tables 1 and 2 of FIG. 4, with most described in detail in previous publications [3-5]. Rough classification of each experiment into like and unlike cell types by a distance ratio cutoff was accurate in 951/961 (99.0%) human and 1250/1296 (96.5%) mouse comparisons, respectively (Charts A and B of FIG. 20). Refining this classifier by using kNN to assign cell types according to the three most similar profiles in the training set resulted in correct predictions for 36/36 mouse and 31/31 human replication timing profiles (Tables C and D of FIG. 20). Strikingly, even closely related cell types could be reliably distinguished using this method, such as mouse ESCs and early primitive ectoderm-like stem cells (EPL/EBM3), and two day intermediates of human ESC differentiation into endomesoderm (DE2; day 2) and definitive endoderm (DE4; day 4). Thus, replication timing profiles appear capable of distinguishing among a wide array of cell types in early mouse and human development.

FIG. 20 shows cell type classification using Monte Carlo-selected domains. Charts A and B show distribution of distances within (darker) and between (lighter) all human replication timing profiles for consensus fingerprinting domains in human (Chart A) and mouse (B) cell types. Number of classification errors as a function of distance ratio cutoff. The optimal classifier (h) is that which minimizes classification errors, with distances above h hypothesized to originate from different cell types. Tables C and D show the classification of human datasets and mouse datasets, respectively. The human dataset classification results for the standard kNN method (Standard) leave-one-out cross-validation (LOOCV), and with each cell type excluded from training (LCTO). For LOOCV, each experiment (e.g., BG01ES.R1) is classified using 20 regions selected with that experiment left out. For LCTO, experiments are labeled as the most similar type in the training set, or correctly classified as "Unseen" for distances above h. Experimental replicates are denoted with suffixes "R1," "R2," etc., and are described in Tables 1 and 2 of FIG. 4.

Confirmation and Generalizability of Replication Timing Fingerprints

The use of all experimental data in a selection algorithm often results in overfitting the model to a limited set of observations. For this reason, machine-learning algorithms are commonly trained and tested on different subsets of data (termed cross-validation). To determine whether overfitting is occurring in this selection method and assess the degree to which fingerprinting domains are generally cell type-specific, leave-one-out cross-validation (LOOCV) was performed with each of the available experiments by constructing fingerprints using all but one experimental replicate, and testing classification on the remaining replicate. In all cases (31/31 human, 36/36 mouse), correct predictions in the excluded profile confirmed that fingerprinting regions remained consistent with cell type, and that most cell-line-specific differences were discarded (Table C of FIG. 20, LOOCV column) This was also true for a cell line with only one replicate (mouse 46C neural precursor cells), implying that most of the regions of differential replication timing useful for classification are shared between cell lines.

To simulate the classification of a cell type not yet encountered in the training set, predictions were tested after selecting fingerprinting regions with all replicates of a given cell type excluded (Table C of FIG. 20, LCTO column) This confirmed that most cell types not yet encountered were correctly classified as "unseen" (7/7 cell types in human, 7/9 in mouse). However, two cases in which profiles were ambiguous were between neural precursors (NPCs) and mouse epiblast-like stem cells (EpiSCs, EBM6), suggesting that closely related cell types are more accurately distinguished when examples of each type are included in the training set.

A Replication Timing Fingerprint for Pluripotency

Figure 21:
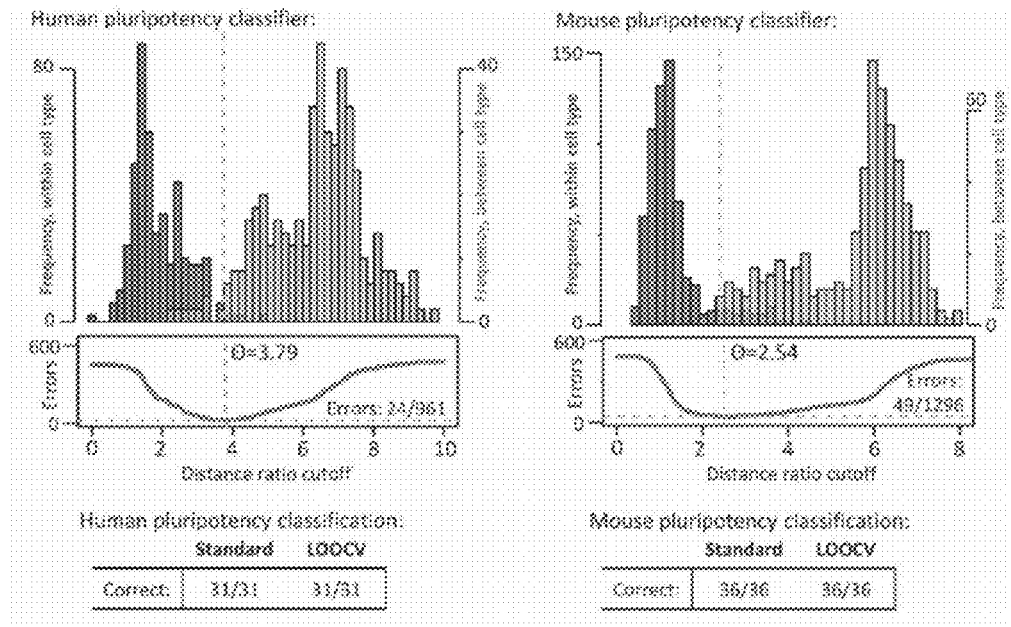
FIG. 21 shows the construction of a general classifier for distinguishing pluripotent from committed mouse and human cell types, with results summarized in the tables for the standard kNN method and leave-one-out cross-validation.

One of the most striking features of replication timing is its widespread consolidation into larger replication domains during neural differentiation, concomitant with global compaction of chromatin [3,4]. This consolidation, along with recovery of ESC replication timing by induced pluripotent stem cells (iPSCs), suggested that replication patterns in specific regions of the genome are associated with the pluripotent state. Further, if certain timing changes are a stable property of cellular commitment, they may provide a unique opportunity to evaluate differentiation capacity using replication-timing patterns. To explore this, the differences in replication timing profiles were analyzed between collections of pluripotent/reversible (ESCs, iPSCs, EBM3) and committed cell types in 13 human and 21 mouse cell lines (FIG. 21). In each case, a stringent consensus fingerprint was created for classification consisting of regions found in >75/100 runs (18 regions each in mouse and human), and examined genes in the top 200 fingerprint regions (~2% of the genome) to characterize a more inclusive sample. Genes and regions found to consistently switch to earlier or later replication as pluripotency is lost are provided in Tables S3, S4, S5, S6 of Ryba T., Hiratani I., Sasaki T., Battaglia D., Kulik M., et al. Replication timing: A fingerprint for cell identity and pluripotency. *PLoS Comput. Biol.* 7(10):e1002225. doi:10.1371/journal.pcbi.1002225 (2011), the entire contents and disclosure of which, including supplementary materials, are incorporated herein by reference.

Figure 22:
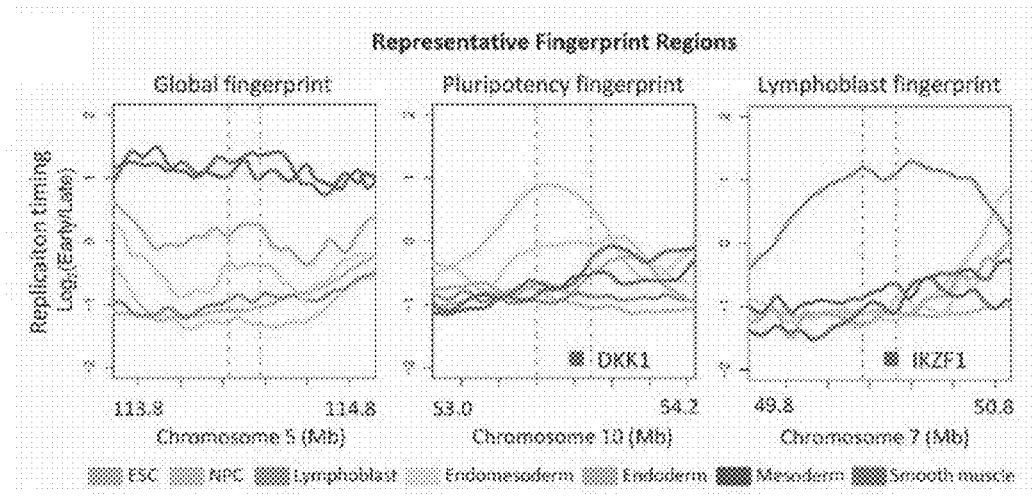
FIG. 22 shows representative fingerprint regions for three cases: general classification (left), distinguishing pluripotent vs. committed cell types (middle), and identifying cell type-specific (here, lymphoblast-specific) regions (right).

FIGS. 21 and 22 show the identification of cell type- and pluripotency-specific regions. FIG. 21 shows the construction of a general classifier for distinguishing pluripotent from committed mouse and human cell types, with results summarized in the tables for the standard kNN method and leave-one-out cross-validation. FIG. 22 shows representative fingerprint regions for three cases: general classification (left), distinguishing pluripotent vs. committed cell types (middle), and identifying cell type-specific (here, lymphoblast-specific) regions (right). Lines represent averaged profiles for each cell type. Several early to late (EtoL) regions in the pluripotency fingerprint contain genes known to function in maintaining stem cell identity, such as Dickkopf homolog DKK1, while uniquely early regions in cell type-specific fingerprints often feature genes with relevant functional or disease associations, such as IKZF1 in lymphoblast cells.

Strikingly, several regions displayed conserved, significant differences in timing between all pluripotent and committed cell types (FIGS. 15, 17 and 21). As with general fingerprints, classification into pluripotent or committed types could be performed unambiguously (36/36 cases in mouse, 31/31 in human), even with regions selected with the test profile excluded (LOOCV column). Several of the genes consistently switching to later replication in mouse and human pluripotency fingerprints have known roles in maintaining pluripotency (for instance, Dppa2 and Dppa4 in both species, and DKK1 in human; see the Tables S4 and S6 of Ryba T., Hiratani I., Sasaki T., Battaglia D., Kulik M., et al. Replication timing: A fingerprint for cell identity and pluripotency. *PLoS Comput. Biol.* 7(10):e1002225. doi:10.1371/journal.pcbi.1002225 (2011), the entire contents and disclosure of which, including supplementary materials, are incorporated herein by reference). In addition, two classes of genes stood out from this analysis that showed significant switches to later replication in both species: a large cluster of protocadherins (PCDs), and the majority of the Hist1 cluster of core histone genes (Table S7 of Ryba T., Hiratani I., Sasaki T., Battaglia D., Kulik M., et al. Replication timing: A fingerprint for cell identity and pluripotency. *PLoS Comput. Biol.* 7(10): e1002225. doi:10.1371/journal.pcbi.1002225 (2011), the entire contents and disclosure of which, including supplementary materials, are incorporated herein by reference). The former are developmentally regulated genes with broad involvement in neural development and cell-to-cell signaling [26,27], and switch to later replication in all committed mouse and human cell types. The latter Hist1 cluster was later replicating in 8/8 committed cell types in mouse and 5/6 in human (not lymphoblasts) and includes several core histone genes that were downregulated up to 2.5-fold in NPCs. These results are intriguing in light of previous reports of histone downregulation during development [28], as well as a hyper-dynamic chromatin phenotype in ESCs that involves higher exchange rates of histone H1 [29] and is required for efficient somatic cell nuclear reprogramming in *Xenopus* oocytes [30]. Importantly, all of the histone H1 genes are found in this cluster, suggesting that regulation of global H1 abundance may provide a mechanism for the overall chromatin compaction and consolidation of replication timing observed during neural differentiation [3-5].

Figure 23:
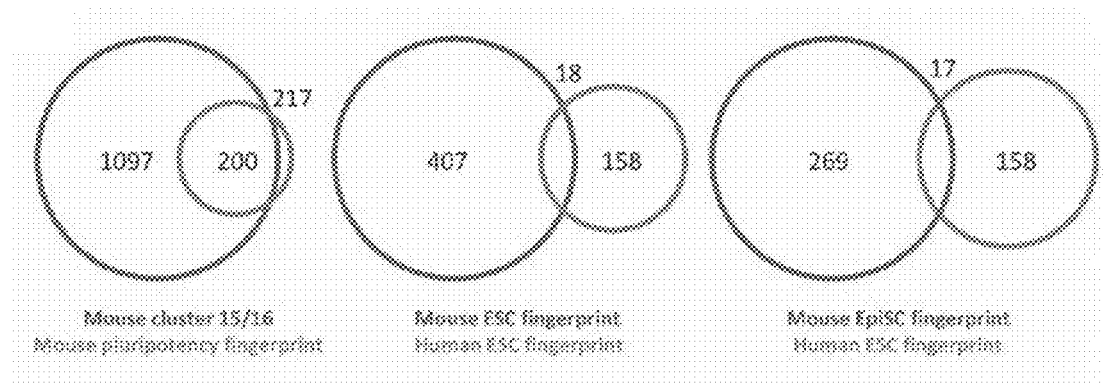
FIG. 23 shows a Venn diagram showing the overlap in genes that fail to reprogram expression in partial iPSCs.

To characterize the genes included in the mouse pluripotency fingerprint, these genes were compared to a previous class of genes that showed lineage-independent switches to later replication in mouse ESC differentiation, and failed to revert to ESC-like expression in three separately derived samples of partial iPSCs (clusters 15 and 16 in FIG. 7 of Hiratani et al., 2010). Remarkably, 200 out of 217 genes in the top 100 mouse pluripotency regions belonged to this class, despite very different methods for deriving them (FIG. 23). All of the fingerprint genes switched to later replication, and at the transition between early and late epiblast stages where cell fates become restricted [5]. Most genes also had reduced expression in late epiblast and neural progenitor stages (average 1.66-fold reduction in transcription from ESC/EBM3 to EBM6/NPCs). Thus, some of these genes may make prime candidates for improving the efficiency of iPSC production, or for reverting human ESCs to a more naïve, mouse ESC-like state. However, the overlap between human and mouse pluripotency fingerprint genes, while significant, was much lower (FIG. 23), and this was true even when comparing human ESCs to developmentally analogous mouse EpiSCs [3,31]. Therefore, many pluripotency-associated genes and loci may be species-specific, consistent with recent studies that underscore considerable differences between mouse and human pluripotency networks [32,33]. This low alignment is also accounted for by a general drop in overall alignment in regions with the greatest developmental switches in replication timing (FIG. 24), which are those preferentially selected by the fingerprinting algorithm.

Figure 24:
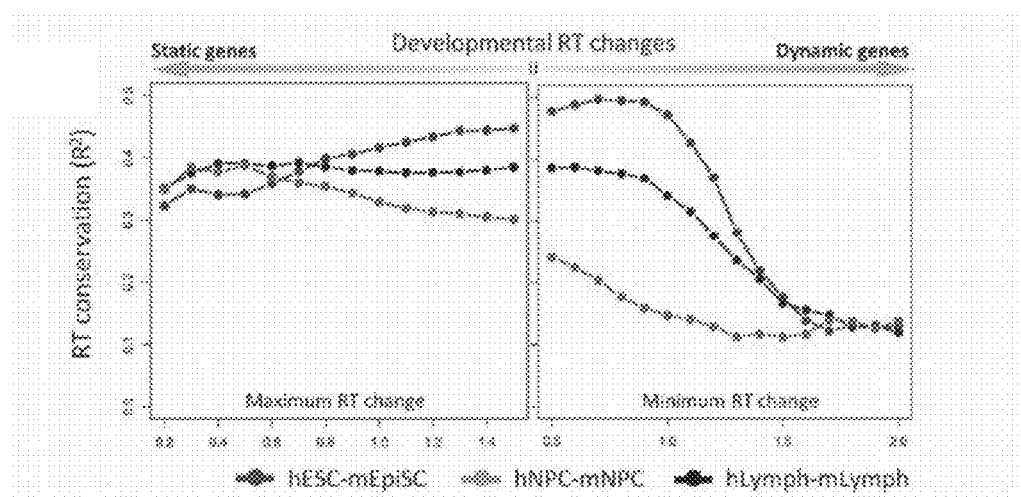
FIG. 24 shows the conservation (R2) of replication timing between human and mouse lymphoblasts (hLymph-mLymph), neural precursors (hNPC-mNPC) and primed stem cells (hESC-mEpiSC) as a function of developmental timing changes.

FIGS. 23 and 24 show the conservation of mouse and human pluripotency fingerprint genes. FIG. 23 shows a Venn diagram showing the overlap in genes that fail to reprogram expression in partial iPSCs (clusters 15 and 16 in Hiratani et al., 2010) and the mouse pluripotency fingerprint (left), between the human and mouse ESC fingerprints (middle), and the human ESC and mouse EpiSC fingerprint (right). FIG. 24 shows the conservation ($R^2$) of replication timing between human and mouse lymphoblasts (hLymph-mLymph), neural precursors (hNPC-mNPC) and primed stem cells (hESC-mEpiSC) as a function of developmental timing changes. For the most closely aligned samples, both relatively static and highly dynamic regions show a decreased alignment in replication timing between species.

Of the genes conserved in the fingerprints of both species (indicated by boldface type in Tables S4 and S6 of Ryba T., Hiratani I., Sasaki T., Battaglia D., Kulik M., et al. Replication timing: A fingerprint for cell Identity and pluripotency. *PLoS Comput. Biol.* 7(10):e1002225. doi:10.1371/journal.pcbi.1002225 (2011), the entire contents and disclosure of which, including supplementary materials, are incorporated herein by reference), most belong to the aforementioned large class of protocadherins. However, Dppa2 and Dppa4 are also conserved, as well as genes with no known roles in maintaining pluripotency (Cast, Riok2, Lix1) that reside within the same replication units as pluripotency fingerprint genes in both species. Other core pluripotency genes remain relatively early replicating in both species (Pou5f1 [Oct4], Sox2, Nanog), and are likely regulated by other mechanisms. For instance, Sox2 belongs to a class of genes with strong promoters (HCP, or high CPG content promoters) generally unaffected by local replication timing [4,34].

Independent Verification of Fingerprint Classification by PCR

Figure 25:
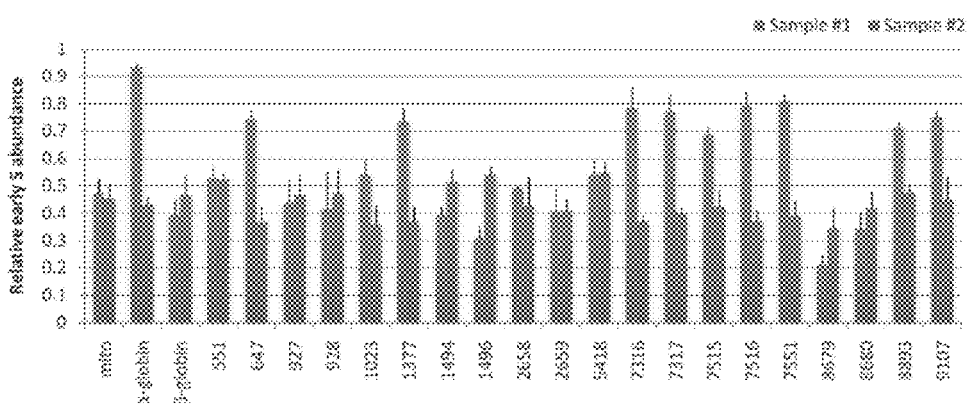
FIG. 25 provides a graph showing replication times for two samples represented by the relative abundance of each sequence in early S phase as a fraction of its abundance in both early and late S phase.
Figure 26:
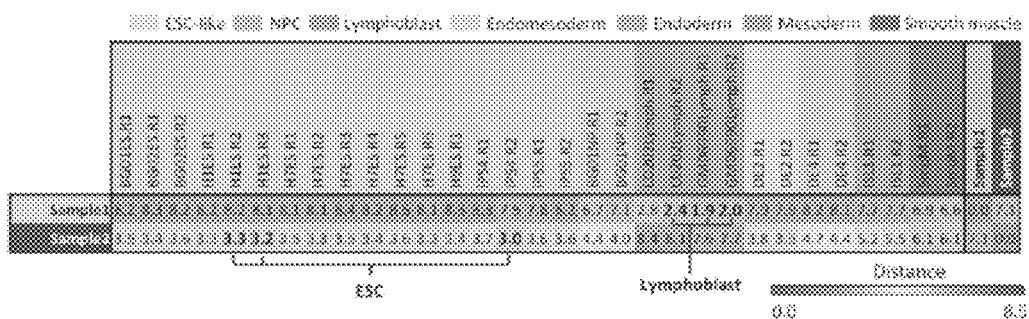
FIG. 26 shows Euclidean distances between replication timing profiles measured in fingerprint regions.

One potential application of replication timing fingerprints is in the development of polymerase chain reaction (PCR) kits for epigenetic classification, particularly for cell types or disease samples with no known aberrations in transcription or sequence. To confirm that fingerprint regions can be translated into a classification scheme using site-specific PCR, two unknown samples were classified representing cell types that were analyzed previously but were derived from cell lines different from the original set used for training. The experiment was performed in a blind manner in which the experimenter had no prior knowledge of the regions or cell types being tested. Primers were assembled against sequences within 10-20 kb from the center of each fingerprint region, and the replication times of each region were quantified as the "relative early S phase abundance" (relative abundance of a sequence in nascent strands from early S phase), as previously described [35] (FIG. 25). PCR-based timing values were rescaled for consistency with the original scale of the array datasets used in training, and distances were calculated between the unknown samples and other human profiles in fingerprint regions (FIG. 26). Using the same methods as in prior classifications, these distances correctly identified the two unknown samples as lymphoblasts and hESCs, respectively; the three known datasets with the smallest distances were each of the correct cell type.

FIGS. 25 and 26 show independent verification of fingerprint classification by PCR. NC-NC lymphoblasts and WIBR3 hESCs were BrdU labeled, early and late nascent strands were purified as for all other cells, and nascent strands were analyzed blindly by PCR using primers specific to 20 human fingerprint regions and control regions (mito: mitochondrial DNA, α-globin, β-globin). In FIG. 25 replication times are represented by the relative abundance of each sequence in early S phase as a fraction of its abundance in both early and late S phase. Error bars depict the average and SEM for each locus after 6 replicate experiments. FIG. 26 shows Euclidean distances between replication timing profiles measured in fingerprint regions described in Table 4 of FIG. 27, after rescaling PCR values to array scale. Color scale for numbers relates the relative similarity of cell types in fingerprint regions, from highly similar to highly divergent. The three lowest distances used for kNN classification (k=3) are highlighted in bold font, with unknown samples #1 and #2 correctly designated as lymphoblasts and ESCs, respectively using the three shortest distances.

Discussion

Advantages and Caveats of Replication Timing Profiles for Cell Typing

According to one embodiment of the present invention, the method for cell typing through replication timing fingerprinting addresses a well-recognized need for comprehensive methods to assess cellular identity and differentiation potential in stem cell biology. Unlike other molecular markers, replication is regulated at the level of large, multimegabase domains, making comprehensive, genome-wide profiles relatively simple to generate and interpret [36]. In particular, the robust stability of replication timing profiles in stem cells [8], and wide divergence between cell types make them a promising candidate for classification.

While the functional role for the replication program is not yet understood, its conservation between human and mouse cell culture models of development support its functional significance. A substantial correlation has been shown ($R_2$=0.42-0.53) in replication patterns between mouse and human cell types, with timing patterns of embryonic stem cells, neural precursor cells, and lymphoblastoid cells most closely aligned to their cognate in the other species [1,3]. The important role for replication is further corroborated by its remarkably strong link to genome organization [3], and its ability to confirm the mouse epiblast identity of human ESCs genome-wide and with an epigenetic property [3,31].

By comparison, methods for cell typing using DNA methylation, gene expression, histone modifications or protein markers are well suited to some applications [10-16], but may not be informative for certain fractions of the genome, or may rely on genome features that cannot distinguish between similar cell states. Replication timing fingerprinting according to one embodiment of the present invention may be used as a complement to existing cell typing strategies that may be used for samples unsuitable for traditional methods, or for additional confidence in assessing cell identity in cases where this is critical, such as regenerative medicine. One caveat to consider in these applications is that replication timing profiles, similar to other genome-wide methods, are an ensemble aggregate from many cells, making measurement of homogeneity difficult. In addition, as with other supervised classification approaches, the method is informative only for cell types (classes) available during training. However, the fingerprinting method, according to one embodiment of the present invention, is in principle applicable to any data type, and may be modified to select discriminating features in other epigenetic profiles.

A major advantage of the fingerprinting method, according to one embodiment of the present invention, is in selection of a minimal set of regions that allows for classification with a straightforward PCR-based timing assay and a reasonably small set of primers, particularly if only cell type specific regions are examined. Results achieved so far using techniques of the present invention suggest that a standard set of 20 fingerprint loci can be effective for classification, but the number of regions queried can be adjusted based on the confidence level required. The sole requirement for replication profiling is the collection of a sufficient number of proliferating cells for sorting on a flow cytometer. Consistently, just as replication timing fingerprints can be generated for particular cell types or general categories of cells, features of replication timing profiles allow for the creation of disease-specific fingerprints, which may be valuable for prognosis.

Consistent Timing Changes Between Pluripotent and Committed Cell Types

In addition to cell typing applications, replication profiling is informative for basic biological questions. Regions have been identifed that may undergo important organizational changes upon differentiation, which include a class of gene that fail to reverse expression in partial iPSCs, and the majority of mouse and human histone H1 genes. Human lymphoblasts retained early replication in H1 genes, which may be explained by their high rate of proliferation. Since highly developmentally plastic regions (including pluripotency fingerprint regions) are poorly conserved (FIG. 24) the evolutionary conservation of cell type-specific timing patterns must be driven by the moderately changing majority of the genome.

The recent derivation of mouse ESC-like human stem cells with various methods raises an intriguing question [37]: will naïve hESCs align better to mESCs than to mEpiSCs for replication timing as they have for transcription? Although pluripotency is currently assessed by marker gene expression or laborious complementation experiments, replication timing assays in regions uniquely early or late replicating in pluripotent cells provide a tractable method to predict the pluripotency of various cell types, as well as insights into conserved genome organizational changes during differentiation.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLE

Methods

Cell Culture and Differentiation

Mouse replication timing datasets are described in Hiratani et al., 2010. Briefly, mouse embryonic stem cells (ESCs) from D3, TT2, and 46C cell lines were subjected to either 6-day (46C) or 9-day (D3, TT2) neural differentiation protocols to generate neural progenitor cells (NPCs) [4,5]. For D3, intermediates were also profiled after 3 (EBM3) and 6 (EBM6) days of differentiation. Muscle stem cells (myoblast) and induced pluripotent stem cells (iPSCs) reprogrammed from fibroblasts were collected as described for human and mouse [38-40]. For human timing datasets, neural precursors were differentiated from BG01 ESCs as described in Schulz et al., 2004 [3,41]. Lymphoblast cell lines GM06990 and C0202 were cultured as previously described [2,42]. Differentiation of BG02 hESCs to mesendoderm (DE2) and definitive endoderm (DE4) was performed by switching from defined media (McLean et al. [20]) to DMEM/F12+100 ng/mL Activin A 20 ng/mL Fgf2 for two and four days, respectively, with 25 ng/mL Wnt3a added on the first day. Mesoderm and smooth muscle cells were derived by adding BMP4 to DE2 cells at 100 ng/mL.

Generation and Preprocessing of Microarray Datasets

Using custom R/Bioconductor scripts [43,44], microarray data from Hiratani et al. 2008, Hiratani et al. 2010, and Ryba et al., 2010 were normalized to equivalent scales, and averaged in nonoverlapping windows of approximately 200 kb. Additional profiles for human ESCs, definitive endoderm, mesendoderm, mesoderm, and smooth muscle were derived, normalized and scaled equivalently, as described [45]. Profiles shown in FIGS. 1 and 22 were smoothed using LOESS with a span of 300 kb.

Monte Carlo Selection of Fingerprinting Regions

Selection of fingerprint regions was performed as described using custom R/Bioconductor scripts. Regions of non-conserved RT (2000/10994 mouse, 2000/12625 human) were first selected based on standard deviation, then optimized using a Monte Carlo algorithm (FIG. 6). Using the Metropolis-Hastings criterion for Monte Carlo with simulated annealing [23,24], moves are accepted when exp ((dRbest2dR)/T).i, where dR is the distance ratio of the proposed move, dRbest is the current best distance ratio, T is a temperature parameter that decreases geometrically during the simulation, and i is a random number from 0 to 1.

Cell Type Classification

Cell type classification was performed using absolute distances between experiments measured from replication timing in fingerprint regions, using the k-nearest neighbor rule with k=3; i.e., each profile was categorized according to the three nearest profiles. Crossvalidation was performed to select an appropriate value for k, with k=3 chosen as the smallest value that yielded 100% classification accuracy after leave-one-out cross-validation (LOOCV) to allow classification of cell types with fewer replicates. For LOOCV results, each experiment was sequentially left out during Monte Carlo selection, and the resulting regions were used to predict the identity of the excluded experiment. To test prediction on cell types not yet encountered, all profiles for a given cell type were left out during region selection (LCTO), and cell type was predicted using the resulting regions. All data analysis was performed using custom R scripts and Bioconductor packages [43,44].

Cell Type Classification Using PCR

For each fingerprint region depicted in Table 4 of FIG. 27, 10-20 kb from the center of the region was sent to NCBI Primer-Blast to design several PCR primer sets with product sizes of 150-350 bp, using standard parameters. Forward and reverse primer pairs displaying the greatest specificity were chosen. Primer sets were verified for specificity and product size using the In-Silico PCR tool at the UCSC genome browser. PCR reactions were set up using 1.25 ng genomic DNA and 1 µM each of forward and reverse primers in 12.5 µL scaled according to the instructions of Crimson Taq DNA Polymerase (NEB). Thirty-six cycles of PCR (empirically determined to be unsaturated for amplification) were performed according to manufacturer's conditions with annealing temperature of 62° C.

One-third of the reaction was analyzed on a 1.5% agarose gel containing ethidium bromide. The gel was scanned by Typhoon Trio (GE Healthcare) and band intensity was quantified by Image Quant TL (GE Healthcare). After the background was subtracted, signal intensity from the early S fraction was divided by the sum of those from early S and late S fractions from each sample, as described [35]. PCR timing values were converted to array RT scale (root-mean-square equivalent) using the scale function in R, and distances were calculated against other cell types as previously performed.

REFERENCES

The following references are referred to above and/or describe technology that may be used with the present invention and are incorporated herein by reference:

1. Yaffe E., Farkash-Amar S., Polten A., Yakhini Z., Tanay A., et al. Comparative analysis of DNA replication timing reveals conserved large-scale chromosomal architecture. *PLoS Genet.* 6:e1001011 (2010).
2. Woodfine K., Fiegler H., Beare D. M., Collins J. E., McCann O. T., et al. Replication timing of the human genome. *Hum. Mol. Genet.* 13:191-202 (2004).
3. Ryba T., Hiratani I., Lu J., Itoh M., Kulik M., et al. Evolutionarily conserved replication timing profiles predict long-range chromatin interactions and distinguish closely related cell types. *Genome Res.* 20:761-70 (2010).
4. Hiratani I, Ryba T, Itoh M, Yokochi T, Schwaiger M, et al. Global reorganization of replication domains during embryonic stem cell differentiation. *PLoS Biol.* 6:e245 (2008).
5. Hiratani I., Ryba T., Itoh M., Rathjen J., Kulik M., et al. Genome-wide dynamics of replication timing revealed by in vitro models of mouse embryogenesis. *Genome Res.* 20:155-69 (2010).
6. Farkash-Amar S., Lipson D., Polten A., Goren A., Helmstetter C., et al. Global organization of replication time zones of the mouse genome. *Genome Res.* 18:1562-70 (2008).
7. Desprat R., Thierry-Mieg D., Lailler N., Lajugie J., Schildkraut C., et al. Predictable dynamic program of timing of DNA replication in human cells. *Genome Res.* 19:2288-99 (2009).
8. Yokochi T., Poduch K., Ryba T., Lu J., Hiratani I., et al. G9a selectively represses a class of late-replicating genes at the nuclear periphery. *Proc. Natl. Acad. Sci. U.S.A.* 106:19363-68 (2009).
9. Berezney R., Dubey D. D., Huberman J. A. Heterogeneity of eukaryotic replicons, replicon clusters, and replication foci. *Chromosoma* 108:471-84 (2000).
10. Marsit C. J., Koestler D. C., Christensen B. C., Karagas M. R., Houseman E. A., et al. DNA methylation array analysis identifies profiles of blood-derived DNA methylation associated with bladder cancer. *J. Clin. Oncol.* 29:1133-9 (2011).
11. Figueroa M. E., Wouters B. J., Skrabanek L., Glass J., Li Y., et al. Genomewide epigenetic analysis delineates a biologically distinct immature acute leukemia with myeloid/T-lymphoid features. *Blood* 113:2795-804 (2009).
12. Baron U., Türbachova I., Hellwag A., Eckhardt F., Berlin K., et al. DNA methylation analysis as a tool for cell typing. *Epigenetics* 1:55-60 (2006).
13. Sotiriou C., Pusztai L. Gene-expression signatures in breast cancer. *N. Engl. J. Med.* 360:790-800 (2009).
14. Hou J., Aerts J., Hamer B. den, Ijcken W. van, Bakker M. den, et al. Gene expression-based classification of non-small cell lung carcinomas and survival prediction. *PLoS ONE* 5:e10312 (2010).
15. Elsheikh S. E., Green A. R., Rakha E. A., Powe D. G., Ahmed R. A., et al. Global histone modifications in breast cancer correlate with tumor phenotypes, prognostic factors, and patient outcome. *Cancer Res.* 69:3802-9 (2009).
16. Barlési F., Giaccone G., Gallegos-Ruiz M. I., Loundou A., Span S. W., et al. Global histone modifications predict prognosis of resected non small-cell lung cancer. *J. Clin. Oncol.* 25:4358-64 (2007).
17. Voss T. C., Schiltz R. L., Sung M-H., Johnson T. A., John S., et al. Combinatorial probabilistic chromatin interactions produce transcriptional heterogeneity. *J. Cell Sci.* 122:345-56 (2009).

18. Chang H. H., Hemberg M., Barahona M., Ingber D. E., Huang S. Transcriptome-wide noise controls lineage choice in mammalian progenitor cells. Nature 453:544-47 (2008).
19. Efroni S., Melcer S., Nissim-Rafinia M., Meshorer E. Stem cells do play with dice: A statistical physics view of transcription. Cell Cycle 8:43-48 (2009).
20. McLean A. B., D'Amour K. A., Jones K. L., Krishnamoorthy M., Kulik M. J., et al. Activin A efficiently specifies definitive endoderm from human embryonic stem cells only when phosphatidylinositol 3-kinase signaling is suppressed. Stem Cells 25:29-38 (2007).
21. Schübeler D., Scalzo D., Kooperberg C., Steensel B. van, Delrow J., et al. Genome-wide DNA replication profile for Drosophila melanogaster: A link between transcription and replication timing. Nat. Genet. 32:438-42 (2002).
22. Weddington N., Stuy A., Hiratani I., Ryba T., Yokochi T., et al. ReplicationDomain: A visualization tool and comparative database for genomewide replication timing data. BMC Bioinformatics 9:530 (2008).
23. Hastings W. K. Monte Carlo sampling methods using Markov chains and their applications. Biometrika 57:97-109 (1970).
24. Metropolis N., Rosenbluth A. W., Rosenbluth M. N., Teller A. H., Teller E. Equation of state calculations by fast computing machines. J. Chem. Phys. 21:1087 (1953).
25. Cover T., Hart P. Nearest neighbor pattern classification. IEEE Trans. Inf. Theory 13:21-27 (1967).
26. Sano K., Tanihara H., Heimark R. L., Obata S, Davidson M., et al. Protocadherins: A large family of cadherin-related molecules in central nervous system. EMBO J. 12:2249-56 (1993).
27. Angst B. D., Marcozzi C., Magee A. I. The cadherin superfamily: diversity in form and function. J. Cell Sci. 114:629-41 (2001).
28. Gerbaulet S. P., Wijnen A. J. van, Aronin N., Tassinari M. S., Lian J. B., et al. Downregulation of histone H4 gene transcription during postnatal development in transgenic mice and at the onset of differentiation in transgenically derived calvarial osteoblast cultures. J. Cell Biochem. 49:137-47 (1992).
29. Meshorer E., Yellajoshula D., George E., Scambler P. J., Brown D. T., et al. Hyperdynamic plasticity of chromatin proteins in pluripotent embryonic stem cells. Dev. Cell 10:105-16 (2006).
30. Jullien J., Astrand C., Halley-Stott R. P., Garrett N., Gurdon J. B. Characterization of somatic cell nuclear reprogramming by oocytes in which a linker histone is required for pluripotency gene reactivation. Proc. Natl. Acad. Sci. U.S.A. 107:5483-88 (2010).
31. Tesar P. J., Chenoweth J. G., Brook F. A., Davies T. J., Evans E. P., et al. New cell lines from mouse epiblast share defining features with human embryonic stem cells. Nature 448:196-99 (2007).
32. Ginis I., Luo Y., Miura T., Thies S., Brandenberger R., et al. Differences between human and mouse embryonic stem cells. Dev. Biol. 269:360-80 (2004).
33. Heng J-C. D., Orlov Y. L., Ng H-H. Transcription factors for the modulation of pluripotency and reprogramming. Cold Spring Harb. Symp. Quant. Biol. 75:237-44 (2010).
34. Weber M., Hellmann I., Stadler M. B., Ramos L., Pääbo S., et al. Distribution, silencing potential and evolutionary impact of promoter DNA methylation in the human genome. Nat. Genet. 39:457-66 (2007).
35. Hiratani I., Leskovar A., Gilbert D. M. Differentiation-induced replication-timing changes are restricted to AT-rich/long interspersed nuclear element (LINE)-rich isochores. Proc. Natl. Acad. Sci. U.S.A. 101:16861-66 (2004).
36. Pope B. D., Hiratani I., Gilbert D. M. Domain-wide regulation of DNA replication timing during mammalian development. Chromosome Res. 18:127-36 (2010).
37. Hanna J., Cheng A. W., Saha K., Kim J, Lengner C. J., et al. Human embryonic stem cells with biological and epigenetic characteristics similar to those of mouse ESCs. Proc. Natl. Acad. Sci. U.S.A. 107:9222-7.
38. Takahashi K., Yamanaka S. Induction of pluripotent stem cells from mouse embryonic and adult fibroblast cultures by defined factors. Cell 126:663-76 (2006).
39. Park I-H., Zhao R., West J. A., Yabuuchi A., Huo H., et al. Reprogramming of human somatic cells to pluripotency with defined factors. Nature 451:141-46 (2008).
40. Maherali N., Sridharan R., Xie W., Utikal J., Eminli S., et al. Directly reprogrammed fibroblasts show global epigenetic remodeling and widespread tissue contribution. Cell Stem Cell 1:55-70 (2007).
41. Schulz T. C., Noggle S. A., Palmarini G. M., Weiler D. A., Lyons I. G., et al. Differentiation of human embryonic stem cells to dopaminergic neurons in serum-free suspension culture. Stem Cells 22:1218-38 (2004).
42. Koch C. M., Andrews R. M., Flicek P., Dillon S. C., Karaöz U., et al. The landscape of histone modifications across 1% of the human genome in five human cell lines. Genome Res. 17:691-707 (2007).
43. Gentleman R. C., Carey V. J., Bates D. M., Bolstad B., Dettling M., et al. Bioconductor: Open software development for computational biology and bioinformatics. Genome Biol. 5:R80 (2004).
44. R Development Core Team. R: A language and environment for statistical computing. ISBN 3:2673. Vienna, Austria: R Foundation for Statistical Computing (2008).
45. Ryba T., Battaglia D., Pope B. D., Hiratani I., Gilbert D. M. Genome-scale analysis of replication timing: From bench to bioinformatics. Nat. Protoc. 6:870-95 (2011).
46. Ryba T., Hiratani I., Sasaki T., Battaglia D., Kulik M., et al. Replication timing: A fingerprint for cell identity and pluripotency. PLoS Comput. Biol. 7(10):e1002225. (PMID 222028635) (2011).

Techniques that may be useful with methods of the present invention are described in: U.S. Provisional Patent Application No. 60/969,399 to Gilbert et al., entitled, "METHOD FOR IDENTIFYING CELLS BASED ON DNA REPLICATION TIMING PROFILE," filed Aug. 28, 2007; U.S. patent application Ser. No. 12/200,186 to Gilbert et al., entitled, "METHOD FOR IDENTIFYING CELLS BASED ON DNA REPLICATION TIMING PROFILE," filed Aug. 28, 2008; U.S. Provisional Patent Application No. 61/489,467 to Gilbert et al., entitled, "GENOME-SCALE OF REPLICATION TIMING: FROM BENCH TO BIOINFORMATICS", filed May 24, 2011; U.S. patent application Ser. No. 13/479,686 to Gilbert et al., entitled, "GENOME-SCALE ANALYSIS OF REPLICATION TIMING," filed May 24, 2012, the entire disclosure and contents of which are incorporated herein by reference.

While the present invention has been disclosed with reference to certain embodiments, numerous modifications, alterations and changes to the described embodiments are possible without departing from the sphere and scope of the present invention, as defined in the appended claims. Accordingly, it is intended that the present invention not be limited to the described embodiments, but that it have the full scope defined by the language of the following claims and equivalents thereof.

What is claimed is:

1. A method of cell-type identification comprising the following steps:
   (a) generating replication timing profiles for a set of different cell types;
   (b) selecting a set of chosen genomic regions that have different replication timing within a set of different cell types and that include a set of nonoverlapping genomic segments having a size of approximately 150 kb to approximately 250 kb in length by removing the genomic segments that have conserved replication timing between cell types, thereby reducing noise from the probe measurements that are used to generate the replication timing profiles of the set of different cell types;
   (c) randomly selecting half of the chosen genomic regions in the set of chosen genomic regions to form an initial set of selected genomic regions and calculating an initial distance ratio between different cell types, whereby unselected chosen genomic regions form a set of unused regions;
   (d) generating a set of replication timing fingerprint regions which is a subset of genomic regions within the set of chosen genomic regions that has an optimized difference in replication timing between different cell types by running an iterative algorithm on the set of chosen genomic regions comprising: starting the iterative algorithm on the initial set of selected genomic regions, randomly selecting one of the following three moves: (i) adding an unused region into the set of selected genomic regions, (ii) removing a region from the set of selected genomic regions so that the region removed becomes an unused region, and (iii) swapping regions between the selected genomic regions and the unused regions, and ending the iterative algorithm when the set of selected genomic regions has a maximized distance ratio between different cell types and a region number decreased to a predetermined minimum;
   (e) generating replication timing fingerprints of known cell types based on the probe measurements in the set of replication timing fingerprint regions generated in step (d);
   (f) measuring replication timing fingerprints of unknown sample cells based on the probe measurements in the set of replication timing fingerprint regions generated in step (d); and
   (g) identifying a cell type of the unknown sample cells by comparing the replication timing fingerprints of the unknown sample cells measured in step (f) to the replication timing fingerprints of known cell types generated in step (e).

2. The method of claim 1, wherein the initial set of selected genomic regions is selected randomly from the set of chosen genomic regions by a computer running the iterative algorithm.

3. The method of claim 1, wherein the set of chosen genomic regions is selected from a set of nonoverlapping genomic segments having a size of approximately 180 kb to approximately 220 kb in length.

4. The method of claim 1, wherein step (c) is conducted by a computer.

5. The method of claim 1 wherein steps (b), (c), (d) and (g) are conducted on a computer.

6. The method of claim 1, wherein the set of chosen genomic regions is selected from a set of nonoverlapping genomic segments having a size of approximately 200 kb in length.

7. The method of claim 1, wherein the predetermined minimum is 20.

8. The method of claim 1, wherein replication timing fingerprints of unknown sample cells are measured through a polymerase chain reaction-based timing assay with a set of primers that is specific to the set of replication timing fingerprint regions.

9. A non-transitory machine-readable medium having stored thereon a series of instructions, which when executed by one or more processors, cause one or more electronic devices to perform a set of operations for cell-type identification comprising the following steps:
  (a) receiving replication timing profiles for a set of different cell types;
  (b) selecting a set of chosen genomic regions that have different replication timing within a set of different cell types and that include a set of nonoverlapping genomic segments having a size of approximately 150 kb to approximately 250 kb in length by removing the genomic segments that have conserved replication timing between cell types, thereby reducing noise from the probe measurements that are used to generate the replication timing profiles of the set of different cell types;
  (c) randomly selecting half of the chosen genomic regions in the set of chosen genomic regions to form an initial set of selected genomic regions and calculating an initial distance ratio between different cell types, whereby unselected chosen genomic regions form a set of unused regions;
  (d) generating a set of replication timing fingerprint regions which is a subset of genomic regions within the set of chosen genomic regions that has an optimized difference in replication timing between different cell types by running an iterative algorithm on the set of chosen genomic regions comprising: starting the iterative algorithm on the initial set of selected genomic regions, randomly selecting one of the following three moves: (i) adding an unused region into the set of selected genomic regions, (ii) removing a region from the set of selected genomic regions so that the region removed becomes an unused region, and (iii) swapping regions between the selected genomic regions and the unused regions, and ending the iterative algorithm when the set of selected genomic regions has a maximized distance ratio between different cell types and a region number decreased to a predetermined minimum;
  (e) generating replication timing fingerprints of known cell types based on the probe measurements in the set of replication timing fingerprint regions generated in step (d);
  (f) measuring replication timing fingerprints of unknown sample cells based on the probe measurements in the set of replication timing fingerprint regions generated in step (d); and
  (g) identifying a cell type of the unknown sample cells by comparing the replication timing fingerprints of the unknown sample cells measured in step (f) to the replication timing fingerprints of known cell types generated in step (e).

10. The machine-readable medium of claim 9, wherein the initial set of selected genomic regions is selected randomly from the set of chosen genomic regions by a computer running the iterative algorithm.

11. The machine-readable medium of claim 9, wherein the set of chosen genomic regions is selected from a set of nonoverlapping genomic segments having a size of approximately 180 kb to approximately 220 kb in length.

12. The non-transitory machine-readable medium of claim 9, wherein steps (b), (c), (d) and (g) are conducted by a computer.

13. The machine-readable medium of claim 9, wherein steps (a), (b), (c), and (f) are conducted by a computer.

14. The non-transitory machine-readable medium of claim 9, wherein the set of chosen genomic regions is selected from a set of nonoverlapping genomic segments having a size of approximately 200 kb in length.

15. The non-transitory machine-readable medium of claim 9, wherein the predetermined minimum is 20.

* * * * *